US012735184B2

(12) United States Patent
Miller

(10) Patent No.: US 12,735,184 B2
(45) Date of Patent: Sep. 15, 2026

(54) METHODS AND SYSTEMS FOR GUIDING POSITION ADJUSTMENT OF A PASSENGER WITH VISUAL IMPAIRMENT IN A TRANSPORTATION VEHICLE

(71) Applicant: Panasonic Avionics Corporation, Irvine, CA (US)

(72) Inventor: Michael Miller, Chino Hills, CA (US)

(73) Assignee: Panasonic Avionics Corporation, Irvine, CA (US)

( * ) Notice: Subject to any disclaimer, the term of this patent is extended or adjusted under 35 U.S.C. 154(b) by 57 days.

(21) Appl. No.: 18/942,188

(22) Filed: Nov. 8, 2024

(65) Prior Publication Data

US 2026/0131893 A1 May 14, 2026

(51) Int. Cl.

*B64D 11/06* (2006.01)
*A61B 3/00* (2006.01)

(52) U.S. Cl.

CPC .......... *B64D 11/064* (2014.12); *A61B 3/0041* (2013.01)

(58) Field of Classification Search

CPC ............................ B64D 11/064; A61B 3/0041
See application file for complete search history.

(56) References Cited

U.S. PATENT DOCUMENTS

| | | | | |
|---|---|---|---|---|
| 2019/0334619 | A1* | 10/2019 | Aoyama | G06V 10/22 |
| 2021/0094471 | A1* | 4/2021 | Krishnamurthi | B60Q 9/00 |
| 2023/0039479 | A1* | 2/2023 | MacIntosh | H04W 4/024 |
| 2023/0332912 | A1* | 10/2023 | Buttolo | G01C 21/3461 |

OTHER PUBLICATIONS

English Translation of DE102022202457A1 Author: Pohlmann et al. Title: Method And System For Finding A Seat In A Passenger Transport Vehicle For People With Impaired Visual Perception Date: Sep. 14, 2023 (Year: 2023).*

* cited by examiner

*Primary Examiner* — Steven Vu Nguyen
(74) *Attorney, Agent, or Firm* — LOZA & LOZA, LLP; Jun S. Ha

(57) ABSTRACT

Methods and systems are provided for a transportation vehicle. One method includes determining a visual impairment parameter indicating a degree of visual impairment of a passenger of a passenger seat associated with the seat device, determining a passenger location of the passenger and a location of a target, estimating an initial facing direction toward which the passenger faces, determining a position adjustment parameter indicating a position adjustment to be made by the passenger of the passenger seat to face the target, based on the passenger location, the location of the target, and the initial facing direction, and outputting a position adjustment instruction according to the position adjustment parameter, the position adjustment instruction including at least an audio instruction in response to the visual impairment parameter indicating visual impairment of the passenger.

20 Claims, 18 Drawing Sheets

Figure 4A:
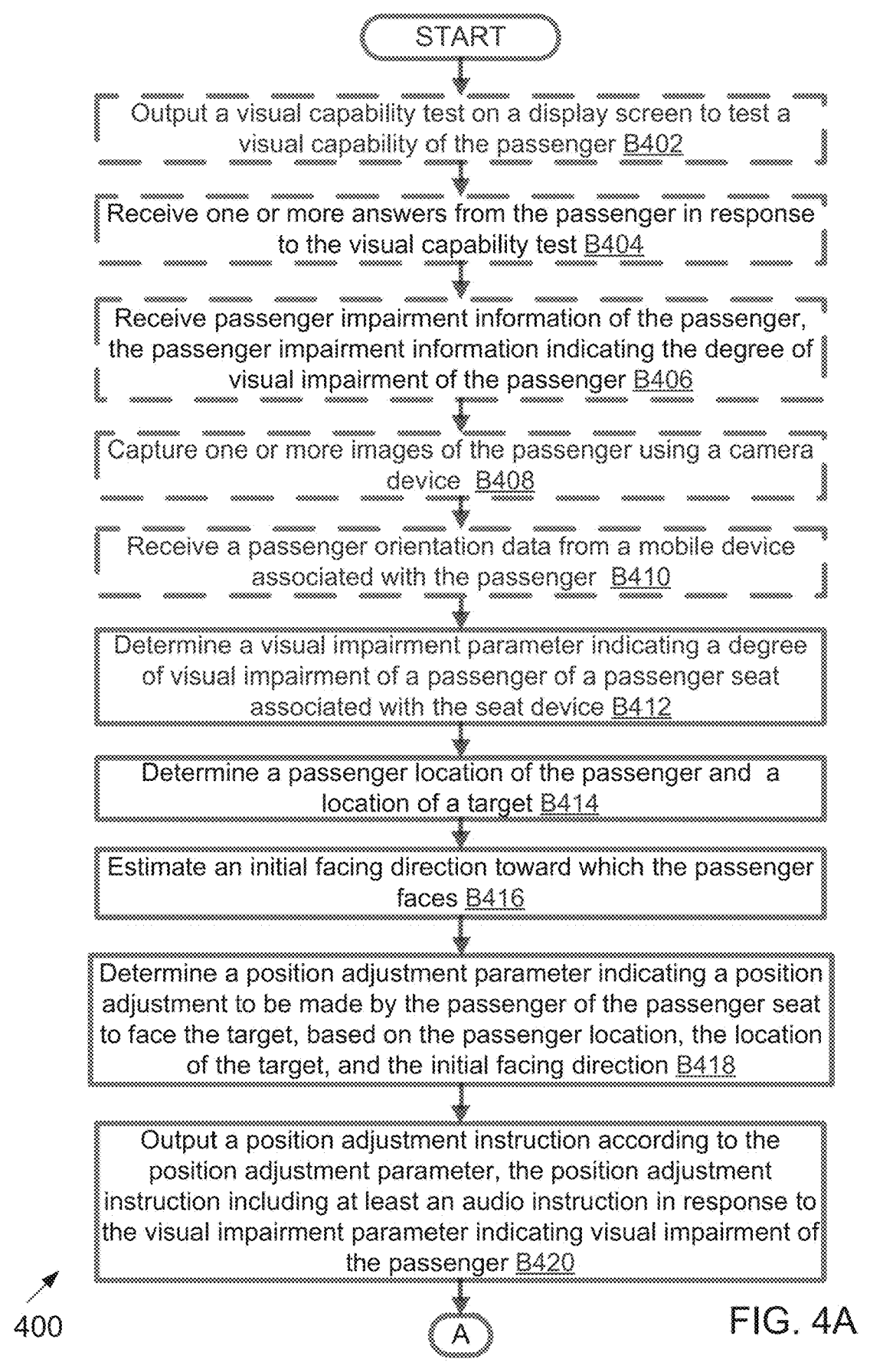

START

Output a visual capability test on a display screen to test a visual capability of the passenger B402

Receive one or more answers from the passenger in response to the visual capability test B404

Receive passenger impairment information of the passenger, the passenger impairment information indicating the degree of visual impairment of the passenger B406

Capture one or more images of the passenger using a camera device B408

Receive a passenger orientation data from a mobile device associated with the passenger B410

Determine a visual impairment parameter indicating a degree of visual impairment of a passenger of a passenger seat associated with the seat device B412

Determine a passenger location of the passenger and a location of a target B414

Estimate an initial facing direction toward which the passenger faces B416

Determine a position adjustment parameter indicating a position adjustment to be made by the passenger of the passenger seat to face the target, based on the passenger location, the location of the target, and the initial facing direction B418

Output a position adjustment instruction according to the position adjustment parameter, the position adjustment instruction including at least an audio instruction in response to the visual impairment parameter indicating visual impairment of the passenger B420

Determine that the passenger has adjusted the position of the passenger further away from a position to face the target after the position adjustment instruction is output B462

Output a visual and hearing capability test on a display screen to test the visual capability and a hearing capability of the passenger in response to the position of the passenger being adjusted further away from the position to face the target B464

Receive at least one answer from the passenger in response to the visual and hearing capability test B466

Determine a hearing impairment parameter indicating a degree of hearing impairment of the passenger and an updated visual impairment parameter of the passenger based on the at least one answer B468

Estimate an updated facing direction toward which the passenger faces after the position adjustment instruction is output B470

Determine an updated position adjustment parameter indicating an updated position adjustment to be made by the passenger to face the target, based on the passenger location, the location of the target and the updated facing direction B472

Output an updated position adjustment instruction based on the updated position adjustment parameter, wherein the updated position adjustment instruction includes at least one of an updated audio instruction or an updated visual instruction, based on the hearing impairment parameter and the updated visual impairment parameter of the passenger B474

METHODS AND SYSTEMS FOR GUIDING POSITION ADJUSTMENT OF A PASSENGER WITH VISUAL IMPAIRMENT IN A TRANSPORTATION VEHICLE

TECHNICAL FIELD

The present disclosure relates to a transportation vehicle and its passenger entertainment device in general, and more particularly, to technology for providing an instruction for position adjustment of a passenger with visual impairment in a transportation vehicle to guide the passenger to face a target.

BACKGROUND

Transportation vehicles, for example, aircraft, trains, buses, recreation vehicle, boats and other similar vehicles use various computing devices for providing various functions, including entertainment, system control, content storage, and other functions. These computing devices include hardware (for example, servers, switches, network interface cards, storage adapters, storage devices and others) and software (for example, server applications, operating systems, firmware, management applications, application programming interface (APIs) and others).

Transportation vehicles, such as airplanes, may have individualized functional equipment dedicated to a passenger seat, which can be utilized by a passenger, such as adjustable seats, adjustable environmental controls, adjustable lighting, telephony systems, video and/or audio entertainment systems, crew communication systems, and the like. For example, many commercial airplanes have individualized video and audio entertainment systems, often referred to as "in-flight entertainment" or "IFE" systems.

Further, it has become quite commonplace for travelers to carry personal electronic devices (PEDs) having wireless communication capability, such as cellular phones, smart phones, tablet computers, laptop computers, and other portable electronic devices. This includes passengers and crew traveling on all types of transportation including the vehicles of common carriers, such as airplanes, passenger trains, buses, cruise ships, sightseeing vehicles (e.g., ships, boats, buses, cars, etc.). Many of these personal electronic devices have the capability to execute application software programs ("apps") to perform various functions, including controlling other devices and systems.

A passenger in a transportation vehicle may desire to face a particular target location. For example, when performing a prayer, a passenger with a particular religion may desire to face a certain location with a religious significance. In an airplane, a seat device at a passenger seat may display a visual representation of the location of the target with respect to a travel direction of the airplane, such that the passenger may adjust the position to face the target by looking at the visual representation. However, the visual representation may not be helpful to a passenger with a certain disability such as visual impairment. Hence, efforts are needed to develop technologies that provide an instruction for position adjustment of a passenger with visual impairment in a transportation vehicle to guide the passenger to face a target.

BRIEF DESCRIPTION OF THE DRAWINGS

The various features of the present disclosure will now be described with reference to the drawings of the various aspects disclosed herein. In the drawings, the same components may have the same reference numerals. The illustrated aspects are intended to illustrate, but not to limit the present disclosure. The drawings include the following Figures:

FIG. 4A shows a process by a seat device of a transportation vehicle for providing an instruction for a passenger to make a position adjustment, according to one aspect of the present disclosure;

FIG. 4C shows a process by the seat device of the transportation vehicle for providing an instruction for the passenger to make a position adjustment, according to one aspect of the present disclosure;

DETAILED DESCRIPTION

In one aspect, innovative technology is disclosed for providing an instruction for a passenger of a transportation vehicle to make a position adjustment, to face a target location. A passenger in a transportation may desire to face a particular target. The transportation vehicle may have a seat device for the passenger, where the seat device may be utilized to provide instructions on how to adjust a position of the passenger to face the target, where the passenger may have a visual impairment. As described below in detail, when the seat device determines that the passenger has a certain degree of visual impairment, the innovative technology determines a position adjustment to be made by the passenger to face the target based on the location of the target and the passenger's initial facing direction, and outputs a position adjustment instruction accordingly at least in audio, to accommodate to the needs of the visually impaired passenger.

As a preliminary note, the terms "component", "module", "system", and the like as used herein are intended to refer to a computer-related entity, either software-executing general-purpose processor, hardware, firmware or a combination thereof. For example, a component may be, but is not limited to being, a process running on a hardware processor, a hardware processor, an object, an executable, a thread of execution, a program, and/or a computer.

By way of illustration, both an application running on a server and the server can be a component. One or more components may reside within a process and/or thread of execution, and a component may be localized on one computer and/or distributed between two or more computers. Also, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal).

Computer executable components can be stored, for example, on non-transitory, computer/machine readable media including, but not limited to, an ASIC (application specific integrated circuit), CD (compact disc), DVD (digital video disk), ROM (read only memory), hard disk, EEPROM (electrically erasable programmable read only memory), solid state memory device or any other storage device, in accordance with the claimed subject matter.

Vehicle Information System

Figure 1A:
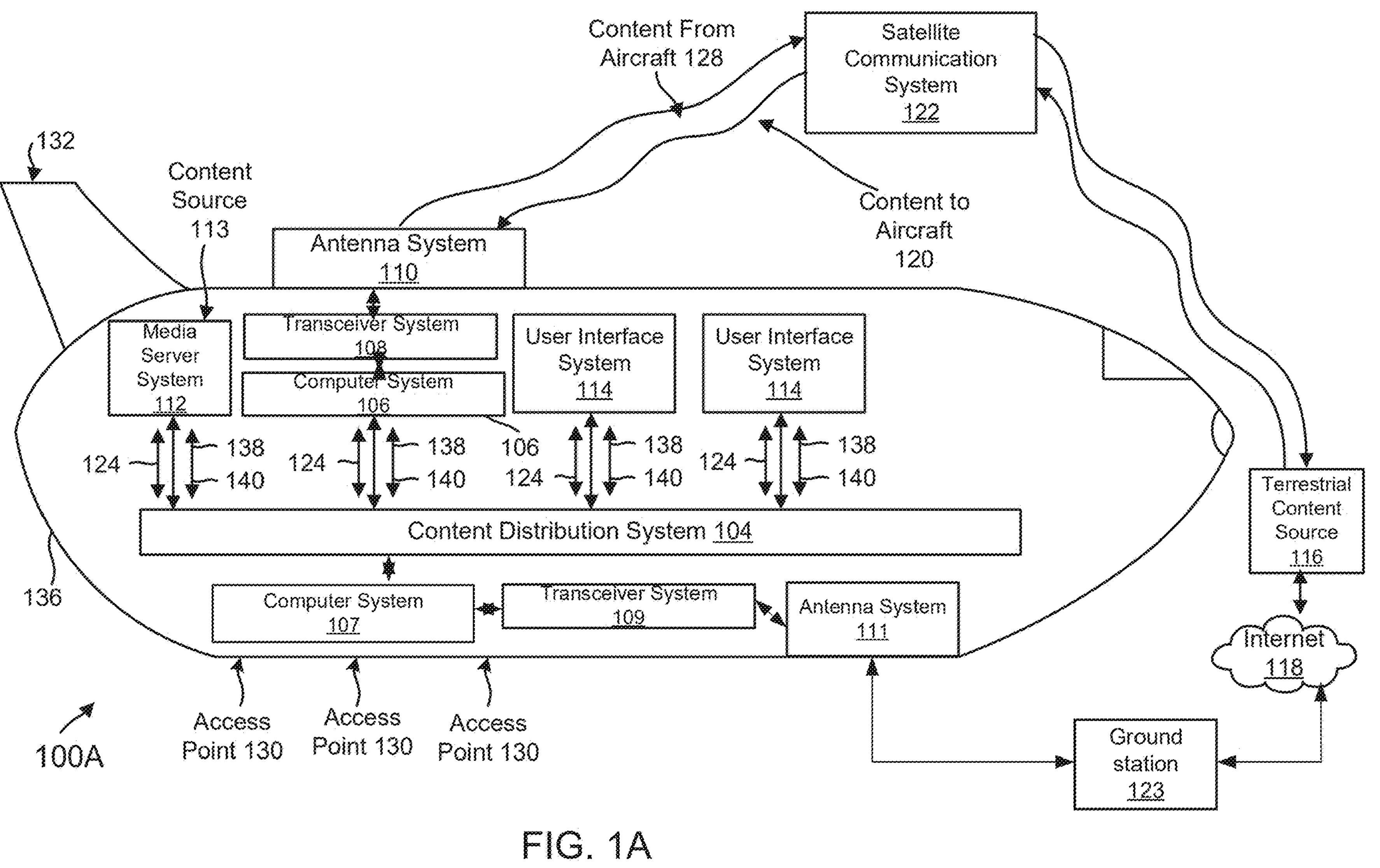
FIG. 1A shows an example of an operating environment for implementing the various aspects of the present disclosure on an aircraft.

FIG. 1A shows an example of a generic vehicle information system 100A (also referred to as system 100A) that can be configured for installation aboard an aircraft 132, according to one aspect of the present disclosure. When installed on an aircraft, system 100A can comprise an aircraft passenger IFE system, such as the Series 2000, 3000, eFX, eX 2, eXW, eX 3, NEXT, and/or any other in-flight entertainment system developed and provided by Panasonic Avionics Corporation (without derogation of any trademark rights of Panasonic Avionics Corporation) of Lake Forest, California, the assignee of this application.

System 100A may include one or more content source 113 and one or more user (or passenger) interface systems (may also be referred to as a seat device/seatback device/IFE device 326 described below with respect to FIG. 3) 114 that communicate with a real-time content distribution system 104.

As an example, the content sources 113 may include one or more internal content sources, such as a media server system 112, that are installed aboard the aircraft 132, one or more remote (or terrestrial) content sources 116 that can be external from the aircraft 132, or a distributed content system. The media server system 112 can be provided as an information system controller for providing overall system control functions for system 100A and/or for storing viewing content 124, including pre-programmed viewing content and/or content 120 downloaded to the aircraft, as desired. The viewing content 124 can include television programming content, music content, podcast content, photograph album content, audiobook content, and/or movie content without limitation. The viewing content as shown and described herein is not exhaustive and are provided herein for purposes of illustration only and not for purposes of limitation.

The server system 112 can include, and/or communicate with, one or more conventional peripheral media storage systems (not shown), including optical media devices, such as a digital video disk (DVD) system or a compact disk (CD) system, and/or magnetic media systems, such as a solid state drive (SSD) system, or a hard disk drive (HDD) system, of any suitable kind, for storing preprogrammed content and/or downloaded content 120.

The viewing content 124 can comprise any conventional type of audio and/or video viewing content, such as stored (or time-delayed) viewing content and/or live (or real-time) viewing content. As desired, the viewing content 124 can include geographical information. Alternatively, and/or additionally, to entertainment content, such as live satellite television programming and/or live satellite radio programming and/or live wireless video/audio streaming, the viewing content likewise can include two-way communications, such as real-time access to the Internet 118 and/or telecommunications and/or a ground station 123 that communicates through an antenna 111 to a transceiver system 109, and a computer system 107 (similar to computer system 106). The functionality of computer system 107 is like computing system 106 for distributing content using the content distribution system 104 described herein. It is noteworthy that although two antenna systems 110/111 have been shown in FIG. 1A, the adaptive aspects disclosed herein may be implemented by fewer or more antenna systems.

Being configured to distribute and/or present the viewing content 124 provided by one or more selected content sources 113, system 100A can communicate with the content sources 113 in real time and in any conventional manner, including via wired and/or wireless communications. System 100A and the terrestrial content source 116, for example, can communicate directly and/or indirectly via an intermediate communication system, such as a satellite communication system 122 or the ground station 123.

System 100A can receive content 120 from a selected terrestrial content source 116 and/or transmit (upload) content 128, including navigation and other control instructions, to the terrestrial content source 116. In one aspect, content 120 includes media content that is stored persistently on the aircraft for passenger consumption. The media content for persistence storage is handled differently than live television content, as described below. As desired, terrestrial content source 116 can be configured to communicate with other terrestrial content sources (not shown). Terrestrial content source 116 is shown as providing access to the Internet 118. Although shown and described as comprising the satellite communication system 122 and the cellular base station 123 for purposes of illustration, the communication system can comprise any conventional type of wireless communication system, such as any wireless communication system and/or an Aircraft Ground Information System (AGIS) communication system.

To facilitate communications with the terrestrial content sources 116, system 100A may also include an antenna system 110 and a transceiver system 108 for receiving the viewing content from the remote (or terrestrial) content sources 116. The antenna system 110 preferably is disposed outside, such as an exterior surface of a fuselage 136 of the aircraft 132. The antenna system 110 can receive viewing content 124 from the terrestrial content source 116 and provide the received viewing content 124, as processed by the transceiver system (may also referred to as broadband controller) 108, to a computer system 106 of system 100A. The computer system 106 can provide the received viewing content 124 to the media (or content) server system 112 and/or directly to one or more of the user interfaces 114 including a PED, as desired. Although shown and described as being separate systems for purposes of illustration, the computer system 106 and the media server system 112 can be at least partially integrated.

The user interface system 114 may be computing terminals in communication with an access point 130. The user interface system 114 provides a display device to view content. The user interface system 114 includes a hardware interface to connect to an access point 130 that provides a wired and/or a wireless connection for the user interface system. In at least one embodiment, the user interface system 114 comprises a software application that a user downloads and installs on a PED to receive and view content via a wireless access point 130. While bandwidth limitation issues may occur in a wired system on a vehicle, such as an aircraft 132, in general the wired portion of the vehicle information 100A system is designed with enough bandwidth to support all users aboard the vehicle, i.e., passengers.

The user interface system 114 can include an input system (not shown) for permitting the user (or passenger) to communicate with system 100A, such as via an exchange of control signals 138. For example, the input system can permit the user to input one or more user instructions 140 for controlling the operation of system 100A. Illustrative user instructions 140 can include instructions for initiating communication with the content source 113, instructions for selecting viewing content 124 for presentation, and/or instructions for controlling the presentation of the selected viewing content 124. If a fee is required for accessing the viewing content 124 or for any other reason, payment information likewise can be entered via the input system. The input system can be provided in any conventional manner and typically includes a touch screen, application programming interface (API), one or more switches (or pushbuttons), such as a keyboard or a keypad, and/or a pointing device, such as a mouse, trackball, or stylus.

In one aspect, the user interface system 114 is provided on individual passenger seats of aircraft 132. The user interface system 114 can be adapted to different aircraft and seating arrangements and the adaptive aspects described herein are not limited to any specific seat arrangements or user interface types.

Figure 1B:
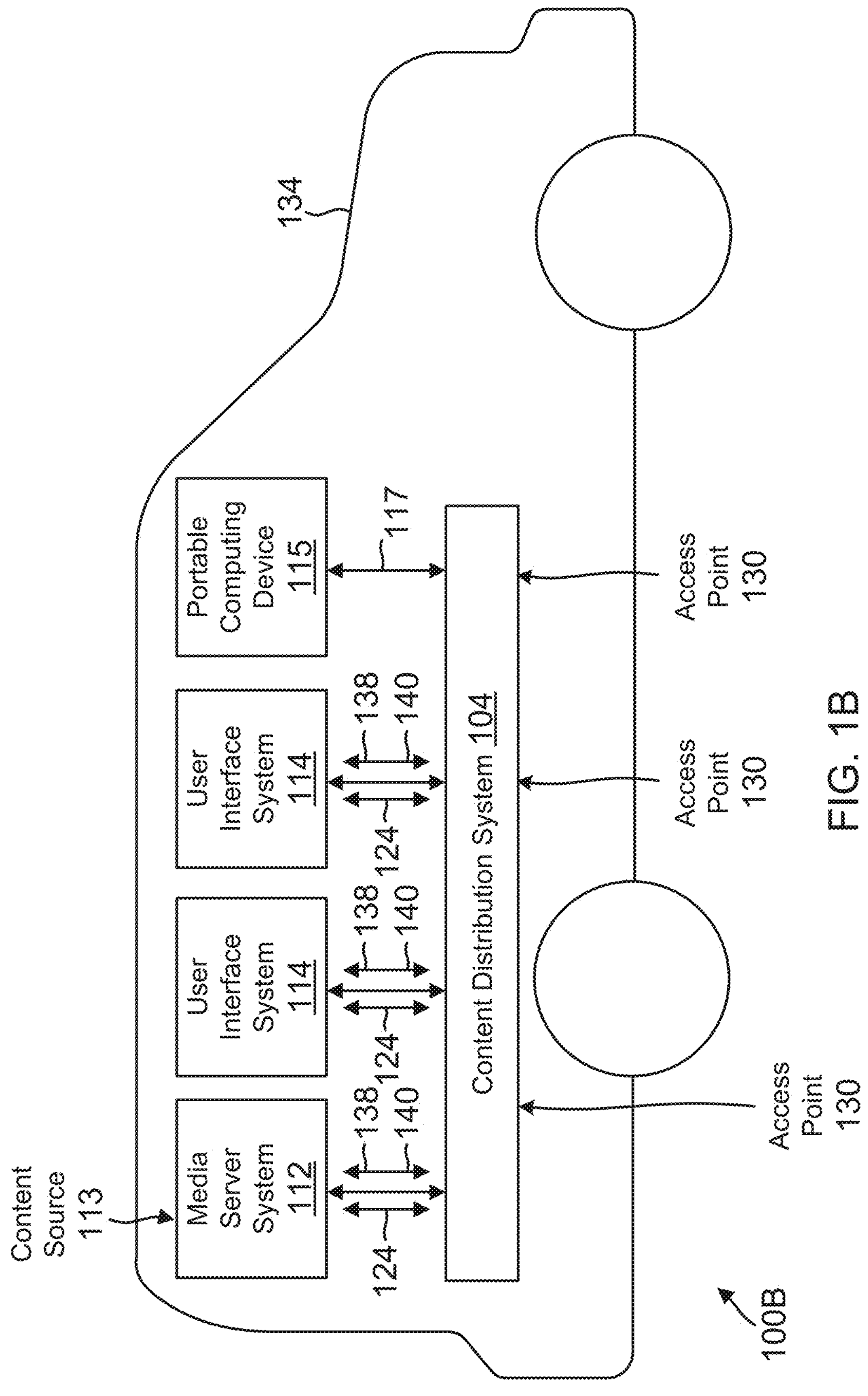
FIG. 1B shows an example of the operating environment on a non-aircraft transportation vehicle type, according to one aspect of the present disclosure.

FIG. 1B shows an example of implementing the vehicle information system 100B (may be referred to as system 100B) on an automobile 134 that may include a bus, a recreational vehicle, a boat, and/or a train, or any other type of passenger vehicle without limitation. The various components of system 100B may be like the components of system 100A described above with respect to FIG. 1A and for brevity are not described again.

Content Distribution System

Figure 2:
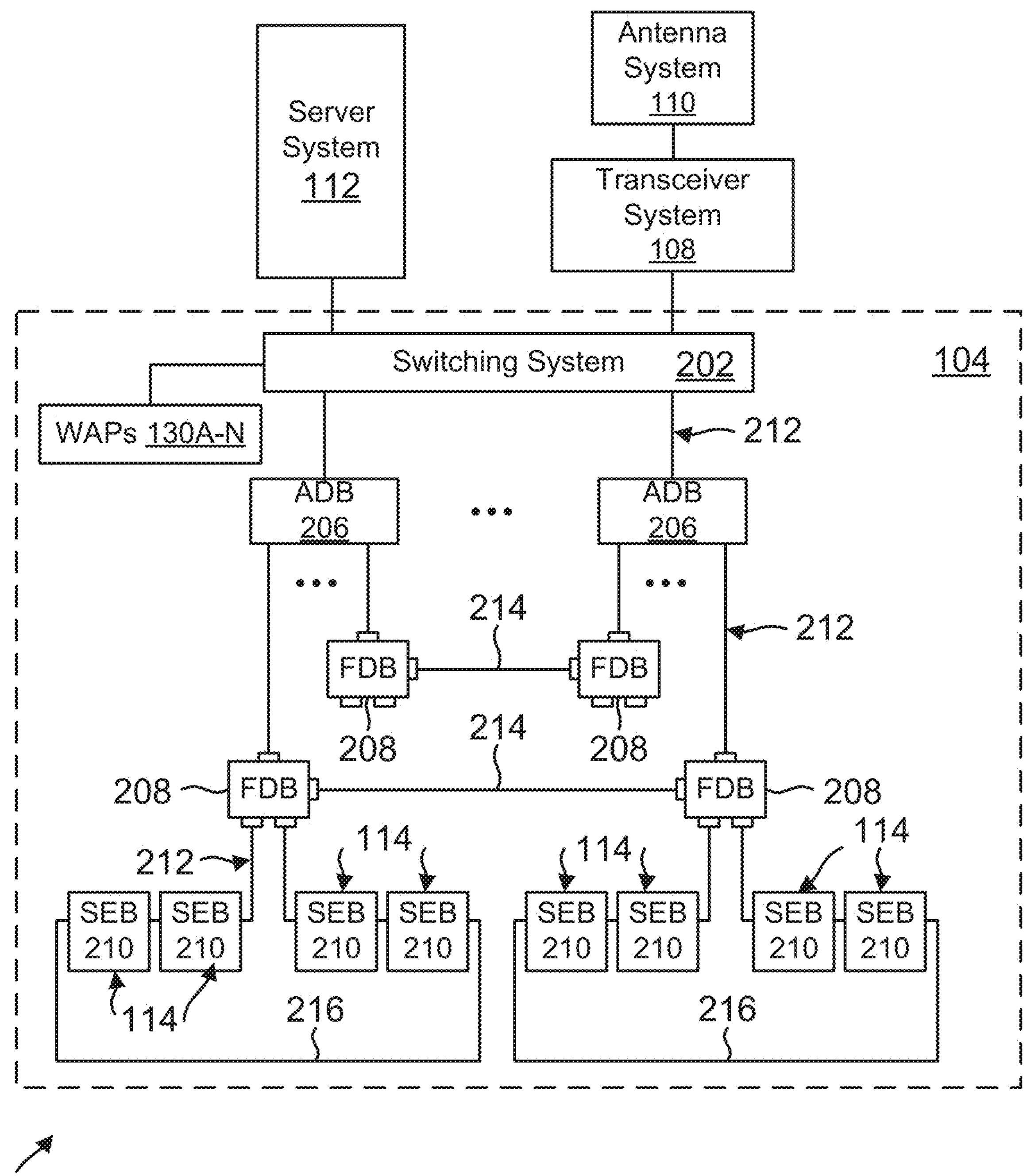
FIG. 2 shows an example of a content distribution system, used according to one aspect of the present disclosure.

FIG. 2 illustrates an example of the content distribution system 104 for the vehicle information system 200 (similar to 100A/100B), according to one aspect of the present disclosure. The content distribution system 104 couples, and supports communication between the server system 112, and the plurality of user interface systems 114. The content distribution system 104, for example, can be provided as a conventional wired and/or wireless communication network, including a telephone network, a local area network (LAN), a wide area network (WAN), a campus area network (CAN), personal area network (PAN) and/or a wireless local area network (WLAN) of any kind. Exemplary wireless local area networks include wireless fidelity (Wi-Fi) networks in accordance with Institute of Electrical and Electronics Engineers (IEEE) Standard 802.11 and/or wireless metropolitan-area networks (MANs), which also are known as WiMax Wireless Broadband, in accordance with IEEE Standard 802.16.

Preferably being configured to support high data transfer rates, the content distribution system 104 may comprise a high-speed Ethernet network, such as any type of Fast Ethernet (such as 100 Base-X and/or 100 Base-T) communication network and/or Gigabit (such as 1000 Base-X and/or 1000 Base-T) Ethernet communication network, with a typical data transfer rate of at least approximately one hundred megabits per second (100 Mbps) or any other transfer rate. To achieve high data transfer rates in a wireless communications environment, free-space optics (or laser) technology, millimeter wave (or microwave) technology, and/or Ultra-Wideband (UWB) technology can be utilized to support communications among the various system resources, as desired.

As illustrated in FIG. 2, the distribution system 104 can be provided as a plurality of area distribution boxes (ADBs) 206, a plurality of floor disconnect boxes (FDBs) 208, and a plurality of seat electronics boxes (SEBs) (and/or video seat electronics boxes (VSEBs) and/or premium seat electronics boxes (PSEBs)) 210 being configured to communicate in real time via a plurality of wired and/or wireless communication connections 212.

The distribution system 104 likewise can include a switching system 202 for providing an interface between the distribution system 104 and the server system 112. The switching system 202 can comprise a conventional switching system, such as an Ethernet switching system, and is configured to couple the server system 112 with the ADBs 206. Each of the ADBs 206 is coupled with, and communicates with, the switching system 202. In addition, the distribution system 104 includes one or more wireless access points (WAPs) (130A to 130N) connected in communication with the switch system 202 for wireless distribution of content to user interface systems 114 including PEDs.

Each of the ADBs 202, in turn, is coupled with, and communicates with, at least one FDB 208. Although the ADBs 206 and the associated FDBs 208 can be coupled in any conventional configuration, the associated FDBs 208 preferably are disposed in a star network topology about a central ADB 206 as illustrated in FIG. 2. Each FDB 208 is coupled with, and services, a plurality of daisy-chains of SEBs 210. The SEBs 210, in turn, are configured to communicate with the user interface systems 114. Each SEB 210 can support one or more of the user interface systems 114.

The switching systems 202, the ADBs 206, the FDBs 208, the SEBs (and/or VSEBs), and/or PSEBs) 210, the antenna system 110 (or 111), the transceiver system 108, the content source 113, the server system 112, and other system resources of the vehicle information system preferably are provided as line replaceable units (LRUs). The use of LRUs facilitate maintenance of the vehicle information system 200 because a defective LRU can simply be removed from the vehicle information system 200 and replaced with a new (or different) LRU. The defective LRU thereafter can be repaired for subsequent installation. Advantageously, the use of LRUs can promote flexibility in configuring the content distribution system 104 by permitting ready modification of the number, arrangement, and/or configuration of the system resources of the content distribution system 104. The content distribution system 104 likewise can be readily upgraded by replacing any obsolete LRUs with new LRUs.

Distribution system 104 can include at least one FDB internal port bypass connection 214 and/or at least one SEB loopback connection 216. Each FDB internal port bypass connection 214 is a communication connection 212 that permits FDBs 208 associated with different ADBs 206 to directly communicate. Each SEB loopback connection 216 is a communication connection 212 that directly couples the last SEB 210 in each daisy-chain of seat electronics boxes 210 for a selected FDB 208 as shown in FIG. 2. Each SEB loopback connection 216 therefore forms a loopback path among the daisy-chained seat electronics boxes 210 coupled with the relevant FDB 208.

It is noteworthy that the various aspects of the present disclosure may be implemented without using FDB 208. When FDB 208 is not used, ADB 206 communicates directly with SEB 210 and/or server system 112 may communicate directly with SEB 210 or the seats. The various aspects of the present disclosure are not limited to any specific network configuration.

System 300

Figure 3A:
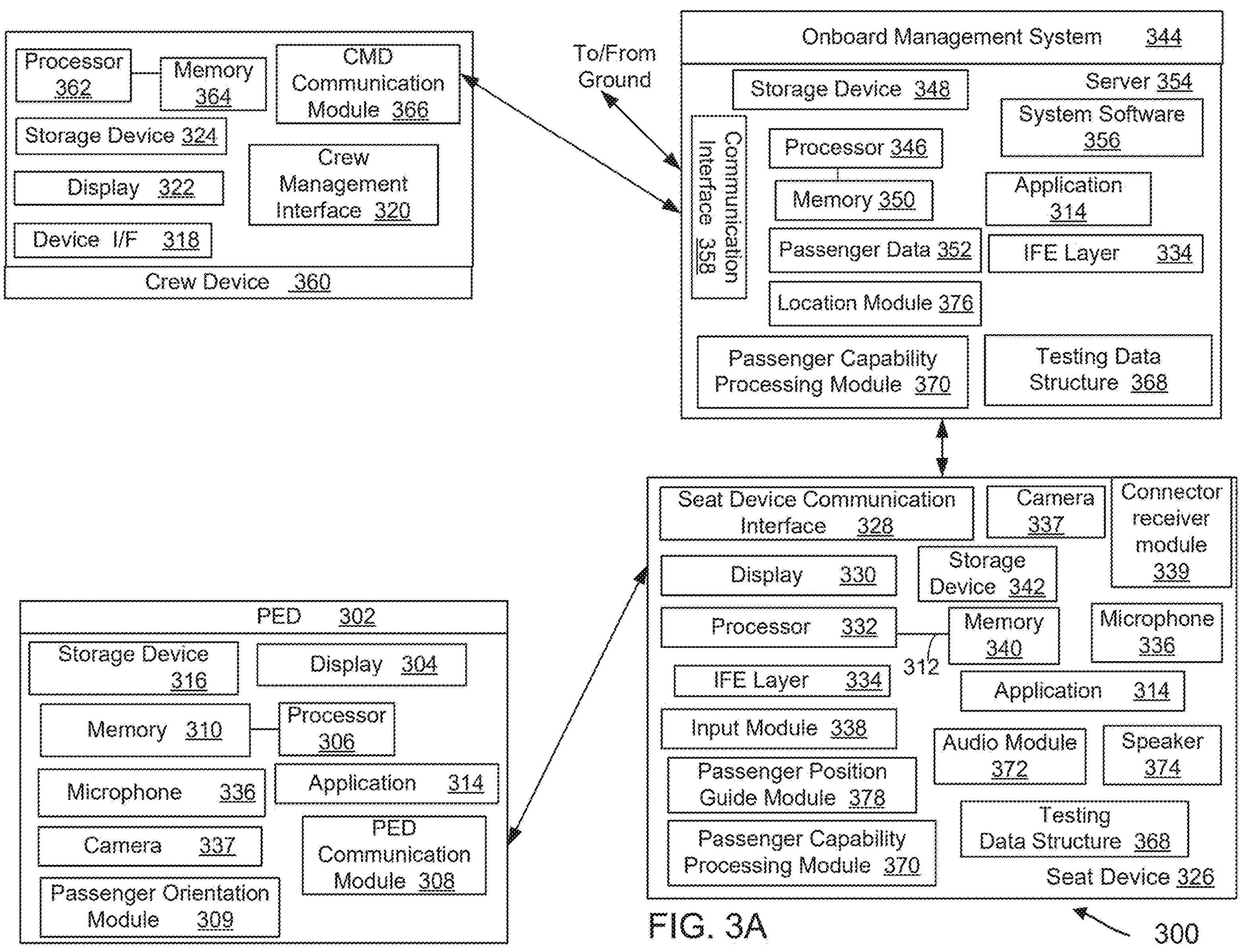
FIG. 3A shows an example of a system for providing an instruction for a passenger to make a position adjustment, according to one aspect of the present disclosure.

FIG. 3A shows an example of a system 300 configured to operate within an aircraft system (e.g., an onboard management system 344 executing an IFE layer, may also be referred to as the IFE system), according to one aspect of the present disclosure. In one aspect, system 300 includes the onboard management system 344 with a server 354, a seat device 326, a PED 302, when authorized, and a crew device (may be referred to as "CMD") 360, when authorized. In yet another aspect, system 300 includes the CMD 360 and the PED 302 or the CMD 360 and the seat device 326, respectively.

In one aspect, the onboard management system 344 includes server 354 (similar to the media server 112 and/or computer system 106/107 described above with respect to FIG. 1A/1B). The server 354 includes a processor 346 that has access to a memory 350 via a bus system/interconnect (similar to 312 on seat device 326). The bus system may represent any one or more separate physical buses and/or point-to-point connections, connected by appropriate bridges, adapters and/or controllers. The bus system may include, for example, a system bus, a Peripheral Component Interconnect (PCI) bus, a PCI-Express bus, a HyperTransport or industry standard architecture (ISA) bus, a small computer system interface (SCSI) bus, a universal serial bus (USB), or an Institute of Electrical and Electronics Engineers (IEEE) standard 1394 bus (sometimes referred to as "Firewire") or any other interconnect type.

Processor 346 may be, or may include, one or more programmable, hardware-based, general-purpose or special-purpose microprocessors, digital signal processors (DSPs), programmable controllers, application specific integrated circuits (ASICs), programmable logic devices (PLDs), or the like, or a combination of such devices.

Processor 346 has access to a storage device 348 that may be used to store data (for example, passenger data 352, applications and program files, including system software 356, application 314, and others). The storage device 348 may further be used to store a testing data structure 368 (may also be referred to as data structure 368) and a passenger capability processing module 370 (may be referred to as module 370) for providing a passenger capability test including a visual capability test and/or hearing capability test to a passenger and for processing the passenger's answers to the passenger capability test to determine results of the passenger capability test. It is noteworthy that module 370 may also be executed at the seat device 326, or any other computing device.

In one aspect, system software 356 is executed by processor 346 to control the overall operation of the server 354. Application 314 may be downloaded from server 354 by passengers using an authorized PED 302 paired with the seat device 326 and/or server 354 for accessing digital content. In an aspect, the PED 302 may be able to communicate with the seat device 326 using the application 314.

In one aspect, the onboard management system 344 maintains flight and passenger data 352 (may also be referred to as data 352), for example, flight itinerary including origin location, layover locations, destination location, arrival time and other information. Data 352 may also include passenger data that identifies each passenger for a flight, a seat assigned to a passenger, a language preference for the passenger, and any other information that can uniquely identify the passengers. Data 352 may further include passenger impairment information for a particular passenger such as a degree of visual impairment and/or a degree of hearing impairment for the particular passenger. Data 352 may be retrieved from a ground system before flight departure. In an aspect, at least some of the information in the data 352 may be entered by a flight crew. In an aspect, the seat device 326 may receive the data 352 from the server 354.

In one aspect, server 354 communicates with CMD 360, PED 302 and/or seat device 326 via the communication interface 358. The communication interface 358 may also be used to receive information from the ground, for example, data 352 and other information. The communication interface 358 includes one or more interfaces for a wired and/or wireless connection, as described above with respect to FIGS. 1A/1B and 2.

In one aspect seat device 326 includes a display device 330, a processor 332, a memory 340, a seat device communication interface (also referred to as communication interface) 328 and a local storage device 342 for storing content. The seat device 326 may optionally include a camera 337 and a microphone 336. The camera may be used to take pictures and videos and the microphone may be used for receiving voice input.

In one aspect, the seat device 326 receives user input/requests via an input module 338. The input module 338 may be configured to use a local touch screen included with display device 330, a local virtual keyboard, an external mouse, external keyboard or any other input device.

In one aspect, processor 332 has access to memory 340 via an interconnect 312. Processor 332 may be, or may include, one or more programmable general-purpose or special-purpose microprocessors, digital signal processors (DSPs), programmable controllers, application specific integrated circuits (ASICs), programmable logic devices (PLDs), or the like, or a combination of such devices.

The bus system 312 is an abstraction that represents any one or more separate physical buses and/or point-to-point connections, connected by appropriate bridges, adapters and/or controllers. The bus system 312, therefore, may include, for example, a system bus, a Peripheral Component Interconnect (PCI) bus, a PCI-Express bus, a HyperTransport or industry standard architecture (ISA) bus, a small computer system interface (SCSI) bus, a universal serial bus (USB), or an Institute of Electrical and Electronics Engineers (IEEE) standard 1394 bus (sometimes referred to as "Firewire") or any other interconnect type.

In one aspect, processor 332 executes an IFE layer 334 out of memory 340. The IFE layer 334 provides in-flight entertainment and other options for users. The IFE layer 334 provides audio/video content as well as controls for accessing the content.

In one aspect, the IFE layer 334 uses the seat device communication interface 328 to interface with the PED 302 and/or onboard management system 344. The communication interface 328 includes logic and circuitry for interfacing with the onboard management system 344 and/or PED 302. In one aspect, the communication interface 328 may use a wireless and/or wired connection for such communication.

In one aspect, processor 332 executes module 370 and maintains data structure 368 that can be used for providing a passenger capability test including a visual capability test and/or hearing capability test to a passenger and managing results of the passenger capability test, as described below.

In one aspect, processor 332 executes passenger position guide module 378 to guide a passenger to adjust a position of the passenger to face a target. In an aspect, the passenger position guide module 378 may output a position adjustment instruction via an audio module 372 and/or the display device 330 to provide the guidance, as described below. The audio module 372 is configured to process and output audio. In an aspect, if the seat device 326 includes a speaker 374, the audio module 372 may output the position adjustment instruction via the speaker 374. In an aspect, the audio module 372 may output the position adjustment instruction to a headset of the passenger, where the headset may be connected to the seat device 326 via a wire or via a wireless communication protocol such as Bluetooth.

In another aspect, the seat device 326 may also execute the application 314 that may be used by the passenger to view media content or various computing functions that are enabled by the seat device 326. Application 314 when executed by the seat device 326 may have different functionality compared to when application 314 is executed by the PED 302.

The seat device 326 on the aircraft may be part of the user interface system 114 or interfaces with the user interface system 114 also described above with respect to FIG. 1A/1B. It is noteworthy that seat device 326 need not be mounted on the back of a seat and may be supported from other structures, such as a bulkhead, wall, arm of a seat, etc. The adaptive aspects of the present disclosure are not limited to any specific location or orientation of the seat device 326.

In one aspect, server 354 communicates with the CMD 360 that may be a mobile phone, a notebook, a tablet, a laptop or any other similar device. CMD 360 may include a processor 362 that has access to a memory 364 via a bus system/interconnect (similar to 312) for executing stored instructions. The bus system may represent any one or more separate physical buses and/or point-to-point connections, connected by appropriate bridges, adapters and/or controllers. The bus system may include, for example, a system bus, a Peripheral Component Interconnect (PCI) bus, a PCI-Express bus, a HyperTransport or industry standard architecture (ISA) bus, a small computer system interface (SCSI) bus, a universal serial bus (USB), or an Institute of Electrical and Electronics Engineers (IEEE) standard 1394 bus (sometimes referred to as "Firewire") or any other interconnect type.

Processor 362 may be, or may include, one or more programmable, hardware based, general-purpose or special-purpose microprocessors, digital signal processors (DSPs), programmable controllers, application specific integrated circuits (ASICs), programmable logic devices (PLDs), or the like, or a combination of such hardware devices.

In one aspect, CMD 360 includes a display 322 to display information. Display 322 may also include a touch screen for receiving input commands. CMD 360 typically includes a microphone (not shown) for receiving voice input. CMD 360 may also include a camera (not shown) for taking pictures or making a video. The CMD 360 may also include a storage device 324 that may include any storage medium for storing data in a non-volatile manner, such as one or more magnetic or optical based disks, flash memory, or solid-state drive. The storage device 316 may be used to store a device interface 318, may also be referred to as a "crew management interface (CMI)" 318 that may be executed out of memory 364.

The CMI 318 enables the CMD 360 to interface with the onboard management system 344 via a CMD communication module 366. The CMD 360 may present one or more APIs to the onboard management system 344 to retrieve passenger/flight data and update data structure 352. The non-limiting API format and syntax will depend on the protocols used by the CMD 360 and the onboard management system 344.

In one aspect, the CMD communication module 366 is also used to communicate with the seat device 326, when installed, and one or more PEDs 302.

In one aspect, the CMD communication module 366 may include one or more interfaces to communicate with different devices, including Wi-Fi interface, Bluetooth interface, NFC (Near Field Communication) interface and others. The adaptive aspects described herein are not limited to any specific interface. It is noteworthy that although a single block is shown for the CMD communication module 366 for convenience, the communication module may have different interface, cards, logic and circuitry to comply with the different communication protocols/standards.

In one aspect, the PED 302 is securely paired with the seat device 326. The term "pair" means that PED 302 is associated and authenticated by the seat device 326 and/or server 354 to send and receive information.

As an example, the PED 302 may be a mobile phone, a notebook, a tablet, a laptop or any other computing device. PED 302 may include a processor 306 that has access to a memory 310 via a bus system/interconnect (similar to 312 on the seat device 326) for executing stored instructions. The bus system may represent any one or more separate physical buses and/or point-to-point connections, connected by appropriate bridges, adapters and/or controllers. The bus system may include, for example, a system bus, a Peripheral Component Interconnect (PCI) bus, a PCI-Express bus, a HyperTransport or industry standard architecture (ISA) bus, a small computer system interface (SCSI) bus, a universal serial bus (USB), or an Institute of Electrical and Electronics Engineers (IEEE) standard 1394 bus (sometimes referred to as "Firewire") or any other interconnect type.

Processor 306 may be, or may include, one or more programmable, hardware based, general-purpose or special-purpose microprocessors, digital signal processors (DSPs), programmable controllers, application specific integrated circuits (ASICs), programmable logic devices (PLDs), or the like, or a combination of such hardware devices.

PEDs 302 may also include a microphone 336 for receiving voice input from a passenger. The voice input can be converted into text by application 314 for processing. In another aspect, PED 302 also includes a camera 337 that may be used by a passenger to upload a video.

PED 302 includes a storage device 316 that may be or may include any storage medium for storing data in a non-volatile manner, such as one or more magnetic or optical based disks, flash memory, or solid-state drive. The storage device 316 may be used to store content displayed on display 304 of PED 302 when used by a passenger. In one aspect, display 304 may include a touch screen for receiving input commands.

The storage device 316 may also store the application 314 that is executed out of memory 310. Application 314 may be used to pair the PED 302 with the aircraft systems to receive content from device 115, as well as to communicate with CMD 360.

As an example, application 314 may be made available for download and installation via a public repository such as that maintained respectively under the trademark GOOGLE PLAY by Google, Inc. and/or the APP STORE maintained by Apple Inc. (without derogation to any third party trademark rights). In addition, application 314 may be provided for download by an airline carrier on a website or from the onboard management system 344.

In one aspect, PED 302 uses a PED communication module 308 to communicate with the seat device 326 and/or CMD 360, when installed. In one aspect, PED communication module 308 may include one or more interfaces to communicate with different devices, including Wi-Fi interface, Bluetooth interface, NFC (Near Field Communication) interface and others. The adaptive aspects described herein are not limited to any specific interface. It is noteworthy that although a single block is shown for the PED communication module 308 for convenience, the communication module may have different interface, cards, logic and circuitry to comply with the different communication protocols/standards.

In one aspect, PED 302 may include a passenger orientation module 309 configured to estimate an orientation of a passenger carrying the PED 302, where the orientation of the passenger may be, for example, a direction the passenger is facing, as described below. The passenger position module 309 may estimate the orientation of the passenger based on a global positioning system (GPS) device and/or a compass device such as a device based on a magnetometer and/or gravity field sensors. In an aspect, the seat device 326 may receive (e.g., via the seat device communication interface 328) a passenger orientation data estimated by the passenger orientation module 309 from the PED 302, as described below.

A passenger in a transportation vehicle such as an aircraft may desire to face a particular target. The target may be in a fixed location, and may be a landmark or a geographical location of a significance or a particular location outside of the aircraft (e.g., location on a map). In one example, when performing Salah prayers, people of the Islamic faith are supposed to position themselves to face the Kaaba, which is a building in Saudi Arabia and is considered a holy site by people of the Islamic faith. Hence, a passenger of an Islamic faith may desire to adjust the position of the passenger to face the Kaaba, even in the transportation vehicle. A visual representation showing the qibla, which is the direction to the Kaaba, may be displayed on the display device 330 of the seat device 326, to guide the passenger to face the Kaaba. Here, the visual representation may show direction to the Kaaba relative to the passenger's current position. When the transportation vehicle is in motion, the transportation vehicle may constantly adjust its travel direction due to various reasons, such as travel path conditions and/or changes in the weather. Consequently, the relative position of the passenger to the Kaaba changes, and thus the qibla also needs to be updated according to the change in the relative position.

Figure 3B:
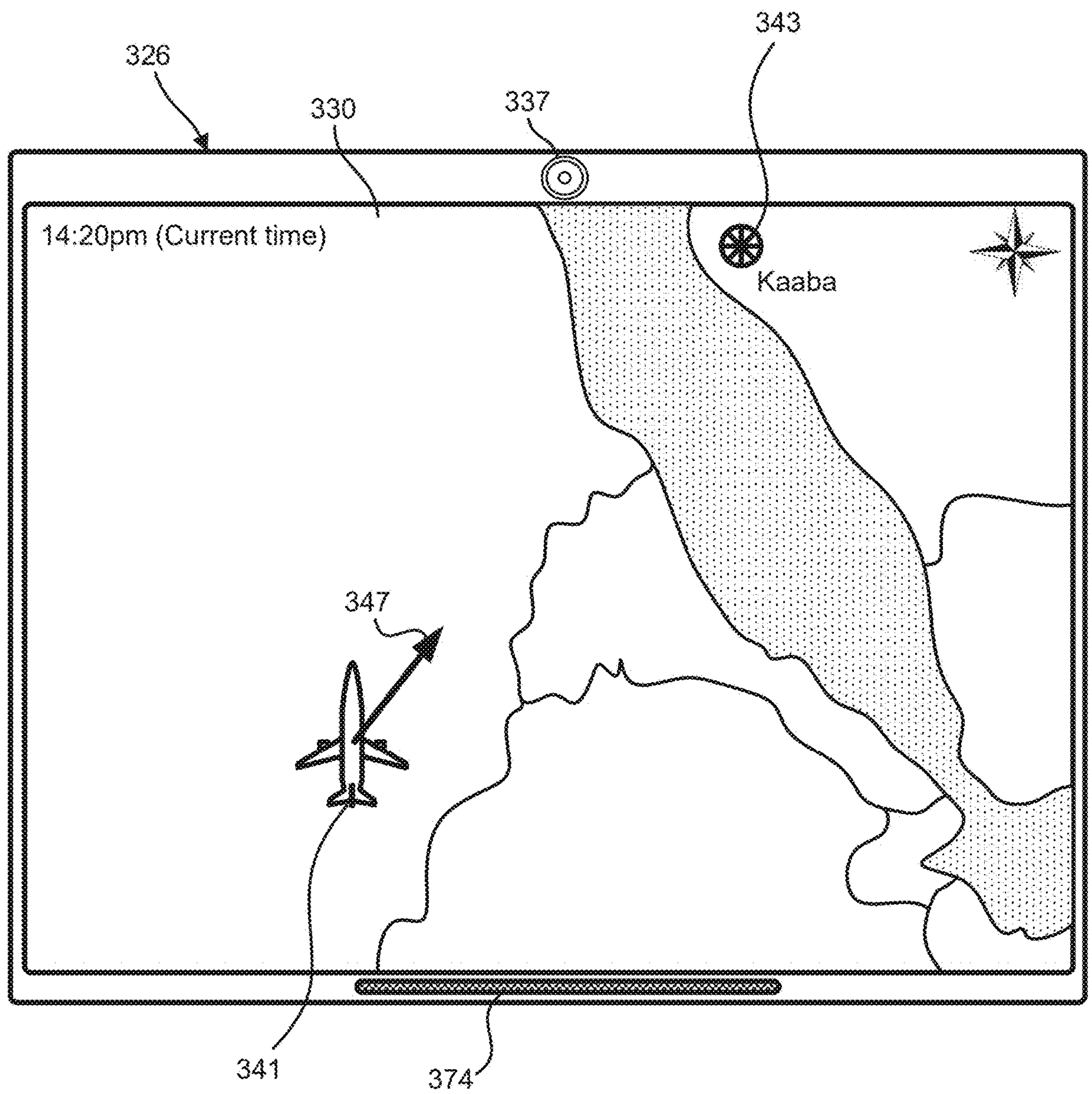
FIG. 3B shows an example of the seat device in a transportation vehicle.

Many seat devices in a transportation vehicle (e.g., aircraft) now have an option to display a map with a location of the transportation vehicle and various locations and land marks. Hence, a passenger may be able to determine how to adjust the position to face a certain location or land mark based on this type of visual representation. FIG. 3B shows an example of the seat device 326 in a transportation vehicle. The example of the seat device 326 in FIG. 3B shows the display device 330, the camera 337, and the speaker 374. In the example of FIG. 3B, the display device 330 of the seat device 326 displays an airplane icon 341 on a map showing a current location and a travel direction of an airplane, and further displays a target icon 343 displaying a location of a particular target, which is the Kaaba in the example shown in FIG. 3B. For example, the current location of the airplane and the location of the particular target may be based on geographic coordinate system (GCS) information (e.g., GCS latitude and longitudinal coordinates). The display device 330 also displays a qibla 347, showing a direction toward the Kaaba. The airplane icon 341 indicates that the travel direction of the airplane is north, and the target icon 343 indicates that the Kaaba is at northeast of the airplane. Based on the visual representations of the airplane icon 341 and the target icon 343, the passenger may easily determine that the passenger needs to turn to right by approximately 30 degrees to face the Kaaba. However, a visually impaired passenger may not be able to comprehend such visual representations, and thus may not be able to correctly adjust the position of the passenger to face the location of the target. Therefore, an approach to guide a passenger with visual impairment to position himself/herself to face a location of a target is desired in a transportation vehicle.

According to some aspects of the disclosure, for a passenger sitting on a seat and using a seat device (e.g., seat device 326) for the seat in a transportation vehicle, the seat device 326 is configured to output a position adjustment instruction that includes at least an audio instruction when the seat device 326 determines that the passenger has a certain degree of visual impairment. The position adjustment instruction may be based on a position adjustment parameter indicating a position adjustment to be made by the passenger of the passenger seat to face the target. Here, the audio instruction may indicate a position adjustment to be made by the passenger of the passenger seat to face the target. In an example, the passenger position guide module 378 of the seat device 326 may generate the position adjustment instruction and utilize the audio module 372 to output the audio instruction, via the speaker 374 or via a headset connected to the seat device 326. As such, the passenger with visual impairment may rely on the audio instruction to adjust the position of the passenger to face the target. In an example, the passenger position guide module 378 of the seat device 326 may generate the position adjustment instruction in text and then utilize a text-to-speech function to output the audio instruction. In some aspects, the passenger position guide module 378 of the seat device 326 may also output, in audio, at least one of the location of the target, a direction of the transportation vehicle, an orientation of the passenger seat associated with the seat device with respect to the transportation vehicle.

To estimate a degree of visual impairment of the passenger, the passenger capability processing module 370 determines a visual impairment parameter indicating the degree of visual impairment of the passenger. For example, if the visual impairment parameter indicates a high number (e.g., 7-10) indicating severe visual impairment, then the passenger position guide module 378 of the seat device 326 may output the position adjustment instruction including at least the audio instruction. In this example, if the visual impairment parameter indicates a low number (e.g., 0-3) indicating little or no visual impairment, then the passenger position guide module 378 of the seat device 326 may output the position adjustment instruction with a visual instruction, and no audio instruction may be output, because the passenger with little or no visual impairment can rely on the visual instruction to determine the position adjustment to be made.

In one example, if the visual impairment parameter indicates a medium number (e.g., 4-6) indicating a mild visual impairment, the passenger position guide module 378 of the seat device 326 may output the position adjustment instruction with both the visual instruction and the audio instruction. Hence, in some aspects, if the visual impairment parameter indicates mild visual impairment of the passenger, then the passenger position guide module 378 of the seat device 326 may output a visual instruction of the position adjustment instruction in addition to the audio instruction.

The passenger position guide module 378 of the seat device 326 determines a passenger location of the passenger and a location of the target and estimates an initial facing direction toward which the passenger faces. Then, the passenger position guide module 378 determines the position adjustment parameter indicating a position adjustment to be made by the passenger of the passenger seat to face the target, based on the passenger location, the location of the target, and the initial facing direction. In some aspects, the passenger location of the passenger may be determined based on the location of the transportation vehicle and a location of the passenger seat within the transportation vehicle, since data on the passenger seat arrangements may be available to the seat device 326. In some aspects, the passenger location may be assumed to be a location of the transportation vehicle. In an example, the passenger position guide module 378 may determine the passenger location and the location of the target based on map data. For example, the passenger location and the location of the target with respect to the passenger location of the passenger may be determined based on the map data and GPS data. For example, the passenger location and the location of the target may be based on geographic coordinate system (GCS) information (e.g., GCS latitude and longitudinal coordinates). In some aspects, the target may be selected by the passenger using the seat device 326.

Further, in some aspects, the position adjustment parameter may indicate which direction to turn and how much to turn to face the target. In an example, the position adjustment parameter may include an angle to turn to face the target. For example, the position adjustment parameter being +45 may indicate that the passenger needs to turn 45 degrees to the left to face the target and the position adjustment parameter being −45 may indicate that the passenger needs to turn 45 degrees to the right.

The visual impairment parameter indicating the degree of visual impairment of the passenger may be determined using one or more of the following approaches. According to one approach, the visual impairment parameter may be determined based on a visual capability test taken by the passenger. The visual capability test may be used to identify a type of assistance best suited for a passenger, based on the test results. In particular, the passenger capability processing module 370 may output (e.g., via the display device 330) a visual capability test on a display screen to test a visual capability of the passenger, and then the passenger may provide answers to the visual capability test, which are received by the passenger capability processing module 370. In one example, the seat device 326 may output the visual capability test that may render various images that show high contrast texts, color inverted texts, magnified texts, and color corrected (e.g., protanomaly, deuteranomaly, and tritanomaly) texts, and then receive answers/feedback from the passenger in response. After the visual capability test is completed and the answers from the passengers are collected, the seat device 326 may optimize the approach for displaying information (e.g., by selecting a particular color and/or increasing a size of the information displayed) on the display device 330. At any time, the passenger may opt out of the test. In this approach, the visual impairment parameter may be determined based on the passenger's answers to the visual capability test.

For example, if the visual impairment parameter for the passenger indicates a severe visual impairment, optimizing the approach for displaying information alone may not be sufficient for the passenger to comprehend the information displayed on the display device 330. Hence, as discussed above, if the visual impairment parameter indicates a severe visual impairment, the seat device 326 may output the position adjustment instruction including at least the audio instruction, such that the visually impaired passenger may rely on the audio instruction to comprehend how to adjust the position to face the target. On the other hand, for example, if the visual impairment parameter indicates a mild visual impairment or a low visual impairment, the seat device 326 may optimize the approach for displaying information (e.g., by selecting a particular color and/or increasing a size of the information displayed), in order to help the passenger comprehend how to adjust the position to face the target.

According to another approach, the visual impairment parameter may be determined based on passenger impairment information of the passenger, which may be provided to the seat device 326. In particular, the passenger capability processing module 370 may receive the passenger impairment information of the passenger, where the passenger impairment information indicates the degree of visual impairment of the passenger, and then may determine the visual impairment parameter based on the passenger impairment information. The passenger capability processing module 370 may receive the passenger impairment information according to one or more of the following approaches. In one approach, the passenger impairment information may be a part of the passenger data 352, which may be received from the server 354 by the seat device 326. As discussed above, the passenger data 352 including the passenger impairment information may be provided to the server 354 from an external system outside the transportation vehicle. In another approach, the passenger impairment information of the passenger may be entered by a crew of the transportation vehicle using the crew device 360 and may be communicated to the seat device 326 through the server 354. For example, the passenger may communicate the passenger's visual impairment degree to the crew, and then the crew may enter the passenger impairment information using the crew device 360. In another approach, the passenger may directly enter the passenger impairment information on the seat device 326 using an input device (e.g., a touch screen, a keyboard, buttons), and the passenger capability processing module 370 may receive the passenger impairment information via the input module 338.

The initial facing direction may be estimated using one or more of the following approaches. An updated facing direction discussed below may also be estimated similarly. According to one approach for estimating the initial facing direction, the passenger position guide module 378 of the seat device 326 may estimate the initial facing direction based on a direction of the transportation vehicle and/or an orientation of the passenger seat associated with the seat device 326 with respect to the transportation vehicle. In an aspect, the information on the orientation of the passenger seat may be provided to the seat device 326 by the server 354. For example, some passenger seats may face the front, other passenger seats may face the back, and other passenger seats may be angled, and thus the initial facing direction of the passenger may be assumed or estimated based on the direction the passenger seat of the passenger is facing. For example, if the transportation vehicle is facing north and the orientation of the passenger seat indicates the passenger seat facing a forward direction and thus faces north, then the seat device 326 may estimate that the initial facing direction is north. In another example, if the transportation vehicle is facing north and the orientation of the passenger seat indicates the passenger seat facing a forward left direction and thus faces northwest, then the seat device 326 may estimate that the initial facing direction is northwest.

According to another approach for estimating the initial facing direction, the seat device 326 may utilize the camera 337 to capturing one or more images of the passenger, and the passenger position guide module 378 of the seat device 326 may estimate the initial facing direction based on the one or more images of the passenger and a direction of the transportation vehicle. For example, the seat device 326 (or the server 354) may perform face detection image processing on the images of the passenger, and estimate which direction the passenger's face is facing based on the face detection image processing. For example, the face detection image processing may be able to estimate which direction the passenger's face is facing based on a distance between a nose and a left ear and a distance between the nose and a right ear, as well as eye sizes and relative lip locations estimated by the image processing. In this approach, when a trip of the passenger on the transportation vehicle ends, the passenger position guide module 378 of the seat device 326 may delete the one or more images upon determining that the trip has ended (e.g., to protect privacy of the passenger).

According to another approach for estimating the initial facing direction, the passenger position guide module 378 of the seat device 326 may receive a passenger orientation data from the PED 302 associated with the passenger, and may estimate the initial facing direction based on the passenger orientation data. In this approach, the passenger orientation module 309 of the PED 302 may determine the passenger orientation data based on an orientation measuring device such as a GPS device and/or a compass device such as a device based on a magnetometer and/or gravity field sensors, and send the passenger orientation data to the seat device 326.

Figure 3C:
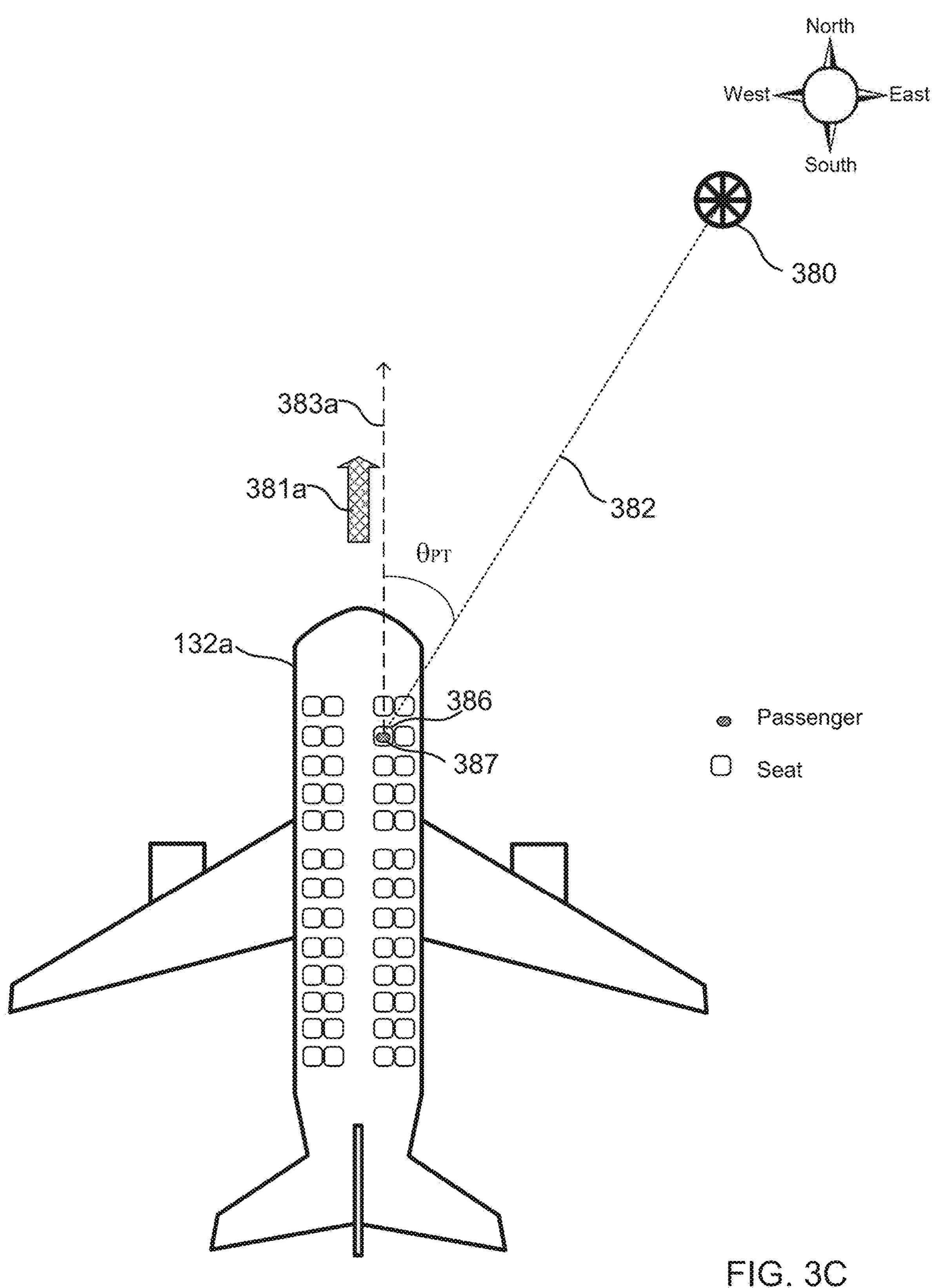
FIG. 3C shows an example diagram showing an aircraft with a passenger facing a forward direction and a target, according to some aspects.

FIG. 3C shows an example diagram showing an aircraft with a passenger facing a forward direction and a target, according to some aspects. In particular, FIG. 3C shows a top view of an aircraft 132*a* and a target 380, where a forward direction 381*a* of the aircraft 132*a* is north. When the aircraft 132*a* is traveling, the forward direction 381*a* is a travel direction of the aircraft 132*a*. The aircraft 132*a* may have the similar features to the aircraft 132 of FIGS. 1A and 1B. The top view of the aircraft 132*a* in FIG. 3C is a transparent view showing passenger seats on the aircraft 132*a*. A passenger seat 386 is occupied by a passenger 387. In this example, the seat device 326 has decided that an initial facing direction 383*a* in which the passenger 387 is initially facing is a forward direction or a travel direction of the aircraft 132*a* (e.g., prior to any position adjustment instruction). In the example of FIG. 3C, all of the seats including the passenger seat 386 are facing the forward direction 381*a* on the aircraft 132*a*. The data on the direction that each passenger seat is facing may be provided to the aircraft 132*b* (e.g., via the server 354 and/or the crew device 360). Based on this data, the seat device 326 may have information on an orientation of the passenger seat 386, which is the forward direction 381*a*. In an example, based on the orientation of the passenger seat 386, the seat device 326 may assume that the passenger 387 is initially facing the forward direction 381*a* of the aircraft 132*a*. In an example, the seat device 326 may capture images of the passenger 387 using a camera device (e.g., camera 337) and then may estimate that the passenger 387 is initially facing the forward direction 381*a* based on the captured images. In an example, seat device 326 may receive passenger orientation data from a mobile device (e.g., PED 302) associated with the passenger 387, and then estimate that the passenger 387 is initially facing the forward direction 381*a* based on the received passenger orientation data.

The passenger 387 needs to face a target facing direction 382, in order to face the target 380. The seat device 326 may determine a passenger location of the passenger 387 and a location of the target 380. In the example of FIG. 3C, based on the passenger location, the location of the target 380, and the initial facing direction 383*a*, the seat device 326 determines that passenger-to-target angle $\theta_{PT}$ between the initial facing direction 383*a* of the passenger 387 and the target facing direction 382 is −30 degrees. Therefore, the passenger 387 needs to turn 30 degrees to the right to face the target 380. In this example, the seat device 326 determines that the position adjustment parameter indicating a position adjustment to be made by the passenger 387 to face the target 380 is −30 degrees, and thus the seat device 326 outputs the position adjustment instruction (e.g., 30 degrees to the right) according to the position adjustment parameter. The position adjustment instruction may be output at least in audio, in response to the visual impairment parameter indicating visual impairment of the passenger 387.

Figure 3D:
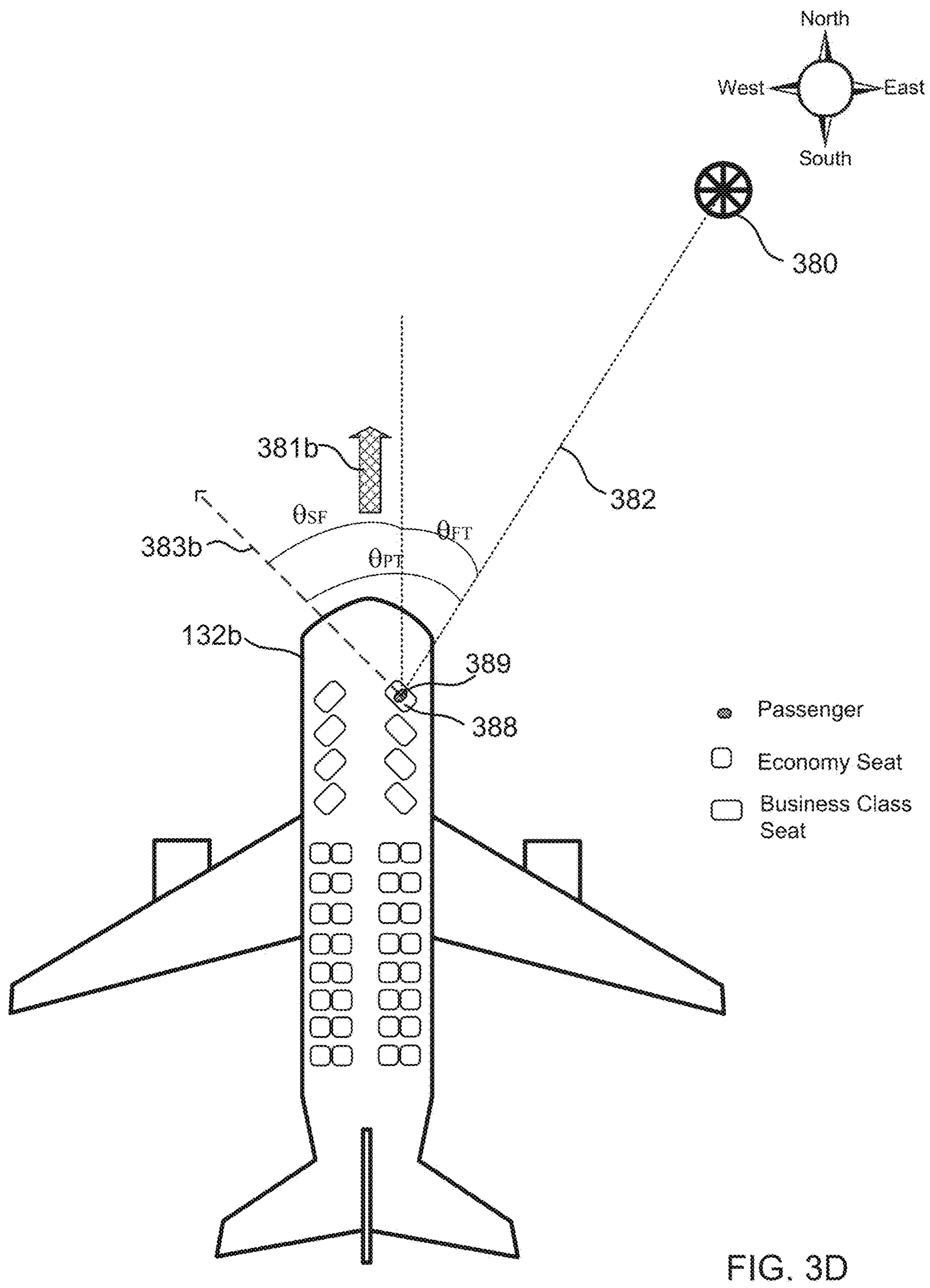
FIG. 3D shows an example diagram showing an aircraft with a passenger facing an angled direction and a target, according to some aspects.

FIG. 3D shows an example diagram showing an aircraft with a passenger facing an angled direction and a target, according to some aspects. In particular, FIG. 3D shows a top view of an aircraft 132*b* and a target 380, where a forward direction 381*b* of the aircraft 132*b* is north. When the aircraft 132*a* is traveling, the forward direction 381*a* is a travel direction of the aircraft 132*a*. The aircraft 132*b* may have the similar features to the aircraft 132 of FIGS. 1A and 1B. The top view of the aircraft 132*b* in FIG. 3D is a transparent view showing economy passenger seats and business class passenger seats on the aircraft 132*a*. A business class passenger seat 388 is occupied by a passenger 389. In the example shown in FIG. 3D, the economy passenger seats are facing the forward direction 381*b* of the aircraft 132*b*, while the business class passenger seats are angled, either facing forward right or forward left. The data on the direction that each passenger seat is facing may be provided to the aircraft 132_b_ (e.g., via the server 354 and/or the crew device 360). Based on this data, the seat device 326 may have information on an orientation of the passenger seat 388, which is facing an initial facing direction 383_b_ angled from the forward direction 381_b_. In an example, based on the orientation of the passenger seat 386, the seat device 326 may assume that the passenger 387 is initially facing the initial facing direction 383_b_ that is angled from the forward direction 381_b_ of the aircraft 132_b_ by a seat-to-forward angle $\theta_{SF}$. In an example, the seat device 326 may capture images of the passenger 387 using a camera device (e.g., camera 337) and then may estimate that the passenger 387 is initially facing the forward direction 381_a_ based on the captured images. In an example, seat device 326 may receive passenger orientation data from a mobile device (e.g., PED 302) associated with the passenger 387, and then estimate that the passenger 387 is initially facing the forward direction 381_a_ based on the received passenger orientation data.

The seat device 326 may determine a passenger location of the passenger 389 and the location of the target 380. The passenger 389 needs to face the target facing direction 382, in order to face the target 380. The seat device 326 may determine that the target facing direction 382 is angled from the forward direction 381_b_ by a forward-to-target angle $\theta_{FT}$, based on the passenger location and the location of the target 380. The forward-to-target angle $\theta_{FT}$ and the seat-to-forward angle $\theta_{SF}$ are added together to determine a passenger-to-target angle $\theta_{PT}$ between the initial facing direction 383_b_ of the passenger 389 and the target facing direction 382. In the example of FIG. 3D, The forward-to-target angle $\theta_{FT}$ is −30 degrees and the seat-to-forward angle $\theta_{SF}$ is −45 degrees, and thus the passenger-to-target angle $\theta_{PT}$ between the initial facing direction 383_b_ of the passenger 389 and the target facing direction 382 is −75 degrees. Therefore, the passenger 389 needs to turn 75 degrees to the right to face the target 380. In this example, the position adjustment parameter indicating a position adjustment to be made by the passenger 389 to face the target 380 is −75 degrees, and thus the seat device 326 outputs the position adjustment instruction (e.g., 75 degrees to the right) according to the position adjustment parameter, where the position adjustment instruction may be output at least in audio, in response to the visual impairment parameter indicating visual impairment of the passenger 389.

After the position adjustment instruction is output, the passenger may have potentially adjusted the position of the passenger. If the passenger has adjusted to a position that faces the target, then the seat device 326 may output a confirmation to confirm that the passenger is facing the target. In particular, after the position adjustment instruction is output, the passenger position guide module 378 of the seat device 326 may estimate an updated facing direction toward which the passenger faces, and may determine whether the passenger faces the target based on the passenger location, the updated facing direction, and the location of the target. If the passenger position guide module 378 of the seat device 326 determines that the passenger faces the target, the passenger position guide module 378 may output a position confirmation at least in audio, to confirm that the passenger is in a position that faces the target.

It may be difficult for the passenger to adjust the passenger position to perfectly face the target. Hence, in some aspects, the passenger position guide module 378 may determine that the passenger faces the target if the passenger faces the target within a predetermined range (e.g., within 2 degrees from the target).

If the passenger position guide module 378 of the seat device 326 determines that the passenger is not facing the target, the passenger position guide module 378 may determine an updated position adjustment parameter indicating an updated position adjustment to be made by the passenger to face the target, based on the passenger location, the location of the target, and the updated facing direction. Then, in some aspects, the passenger position guide module 378 may output either a visual instruction on a display screen based on the updated position adjustment parameter or both the visual instruction and an audio instruction based on the updated position adjustment parameter. If the passenger has not adjusted his position to face the target even after the position adjustment instruction is provided in audio, then it is possible that the passenger may not be able to hear the position adjustment instruction in audio well enough to comprehend, e.g., due to the passenger's hearing impairment and/or faulty speakers on the seat device and/or a noisy environment. In this scenario where the passenger is not facing the target even after the position adjustment instruction is provided in audio, it may be beneficial to provide a visual instruction or both the visual instruction and the audio instruction because the passenger may comprehend an instruction that includes at least the visual instruction better than an instruction that includes only the audio instruction. In another aspect, the passenger position guide module 378 may output only an audio instruction based on the updated position adjustment parameter.

Figure 3E:
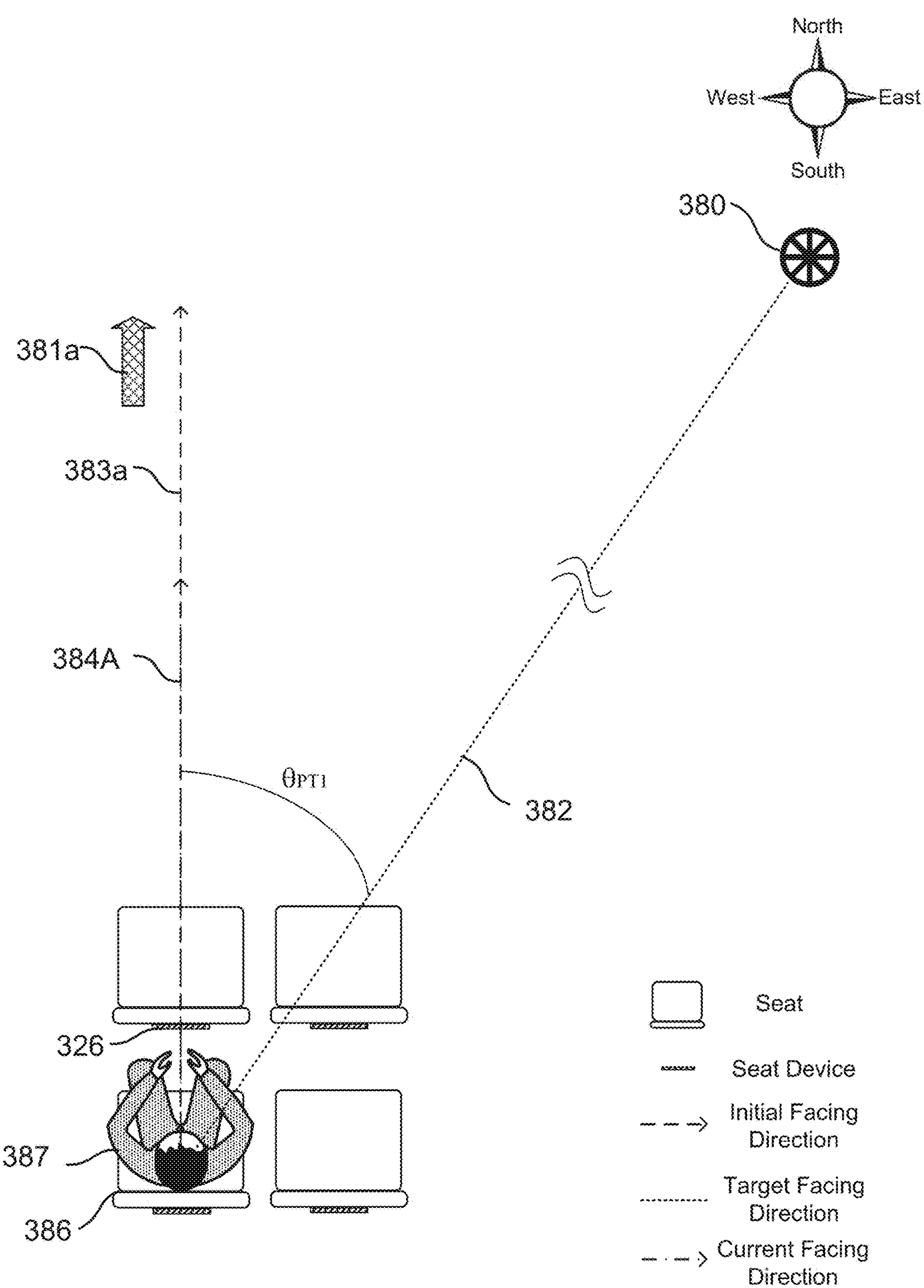
FIG. 3E shows an example diagram showing a passenger sitting on a passenger seat of an aircraft with a passenger facing a forward direction, angled from a target, according to some aspects.

FIGS. 3E-3H show example diagrams showing a passenger facing different directions, according to some aspects. FIG. 3E shows an example diagram showing a passenger sitting on a passenger seat of an aircraft with a passenger facing a forward direction, angled from a target, according to some aspects. FIG. 3E may be an enlarged view showing a portion of FIG. 3C around the passenger 387 sitting on the passenger seat 386 in the aircraft 132_a_. Hence, in FIG. 3E, the passenger 387 is initially facing an initial facing direction 383_a_, which is the same as a current facing direction 384A indicating the direction the passenger 387 is currently facing in FIG. 3E. The initial facing direction 383_a_ is parallel to the forward direction 381_a_ of the aircraft. The passenger 387 is provided with the seat device 326.

A target facing direction 382 may be determined based on a passenger location of the passenger 387 and the location of the target 380. The seat device 326 may determine a position adjustment parameter indicating a position adjustment to be made by the passenger 387 to face the target 380, based on the initial facing direction 383_a_ and the target facing direction 382 that is based on the passenger location and the location of the target 380. As shown in FIG. 3E, the passenger 387 needs to face the target facing direction 382, in order to face the target 380. In the example of FIG. 3E, a passenger-to-target angle $\theta_{PT1}$ between the initial facing direction 384A of the passenger 387 and the target facing direction 382 is −30 degrees. Therefore, the passenger 387 needs to turn 30 degrees to the right to face the target 380. In this example, the position adjustment parameter is −30 degrees, and thus the seat device 326 outputs the position adjustment instruction (e.g., 30 degrees to the right) according to the position adjustment parameter, where the position adjustment instruction may be output at least in audio, in response to the visual impairment parameter indicating visual impairment of the passenger 387.

Figure 3F:
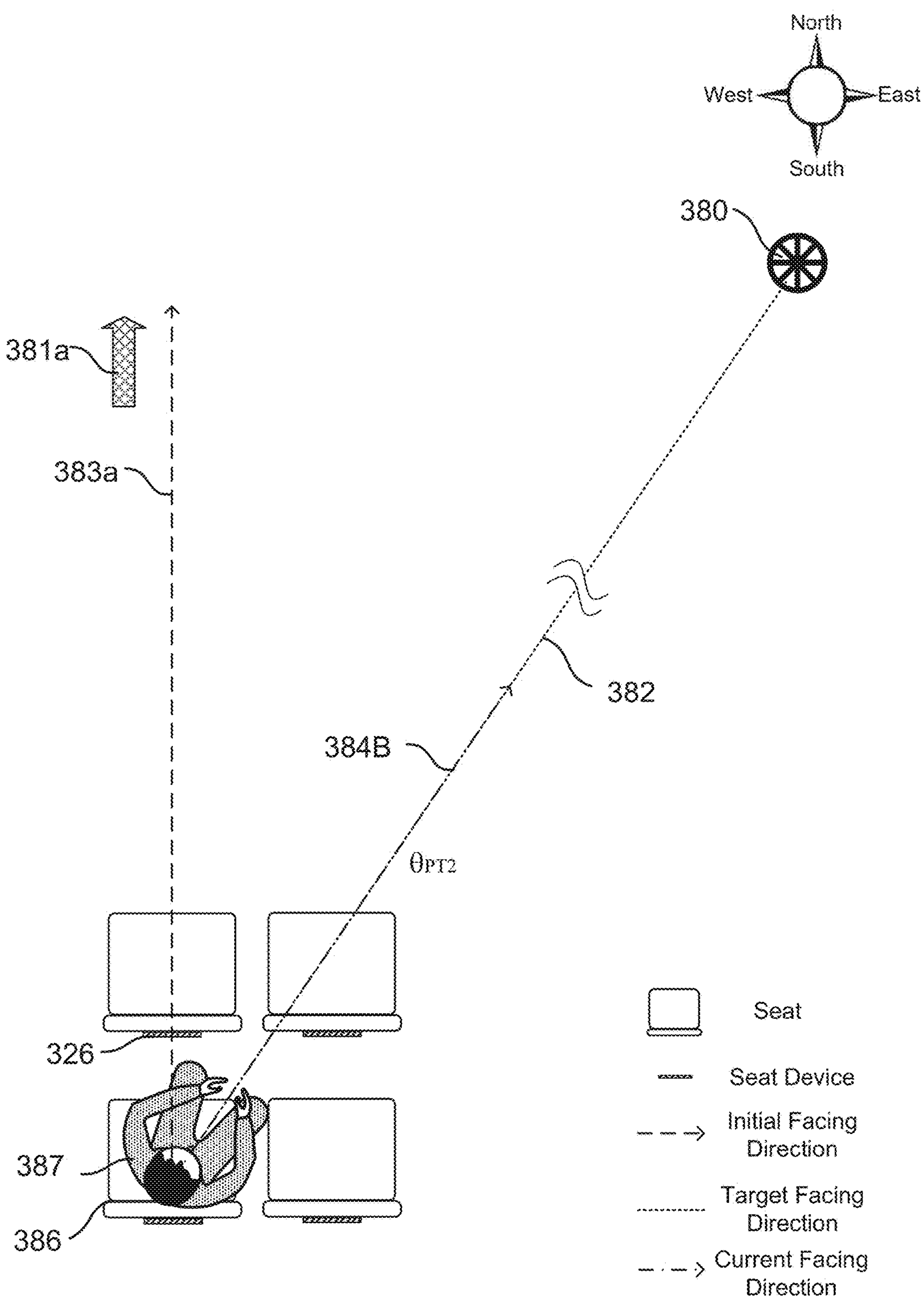
FIG. 3F shows an example diagram showing the passenger of FIG. 3E sitting on the passenger seat with the passenger facing the target, according to some aspects.

FIG. 3F shows an example diagram showing the passenger of FIG. 3E sitting on the passenger seat with the passenger facing the target, according to some aspects. The example shown in FIG. 3F occurs after the seat device 326 outputs the position adjustment instruction in FIG. 3E and the passenger 387 adjusts the passenger's facing direction. In FIG. 3F, the passenger 387 has adjusted the passenger's position to face the target 380, and thus a current facing direction 384B in FIG. 3F aligns or substantially aligns with the target facing direction 382. For example, sometime after outputting the position adjustment instruction in FIG. 3E, the passenger 387 has adjusted the passenger's position. Hence, a passenger-to-target angle $\theta_{PT2}$ between the current facing direction 384B of the passenger 387 and the target facing direction 382 is 0 degree. Then, the seat device 326 in FIG. 3F may estimate the current facing direction 384B (e.g., updated facing direction) and determine that the passenger 387 faces the target 380 based on the passenger location, the current facing direction 384B, and the location of the target 380. As discussed above, in some aspects, the seat device 326 may determine that the passenger 387 faces the target 380 if the passenger 387 faces the target 380 within a predetermined range (e.g., within 2 degrees from the target 380 with respect to the target facing direction 382). Upon this determination, the seat device 326 may output a position confirmation at least in audio, indicating that the passenger 387 is facing the target 380.

Figure 3G:
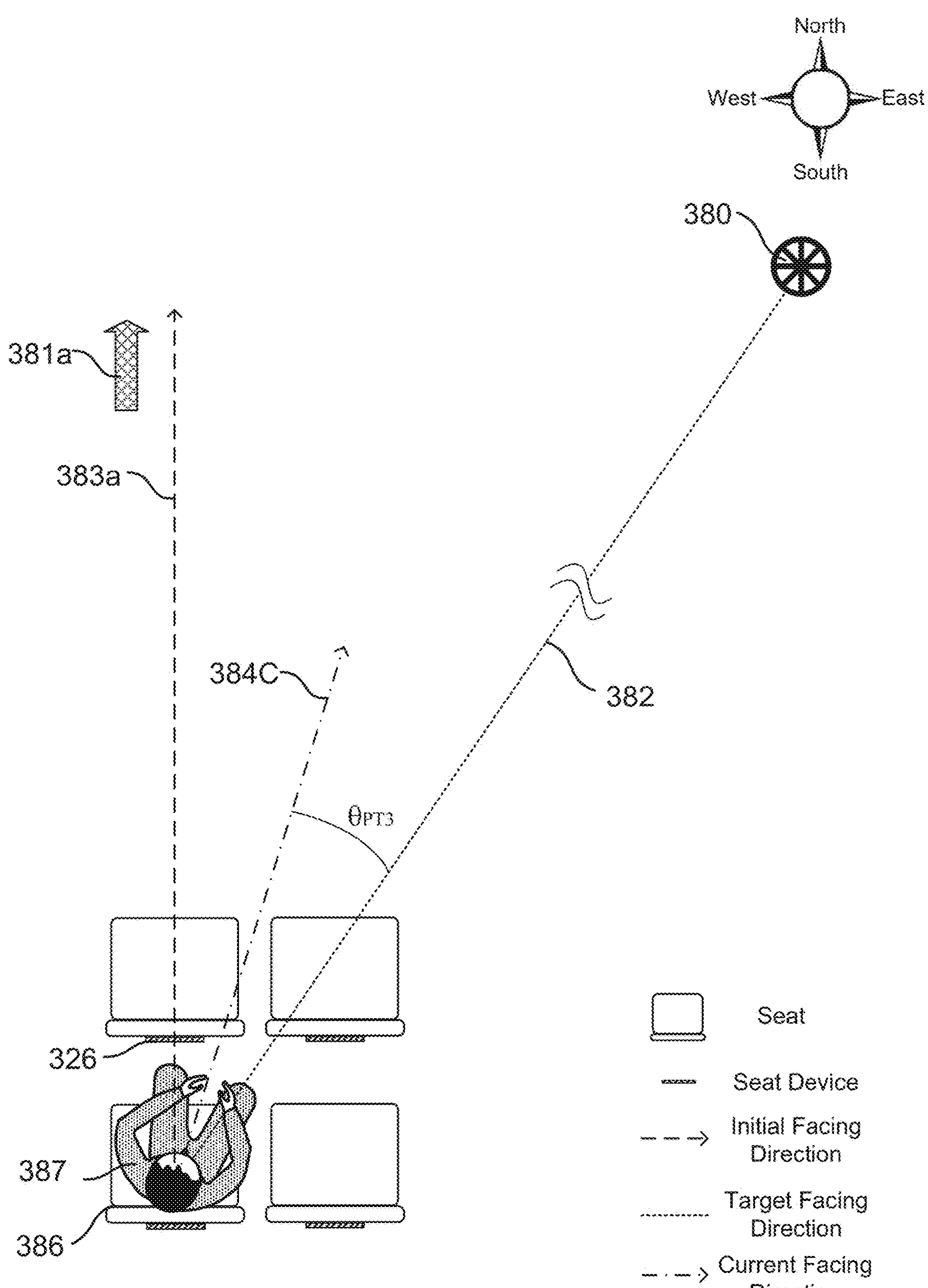
FIG. 3G shows an example diagram showing the passenger of FIG. 3E sitting on the passenger seat with the passenger not facing the target yet, according to some aspects.

FIG. 3G shows an example diagram showing the passenger of FIG. 3E sitting on the passenger seat with the passenger not facing the target yet, according to some aspects. The example shown in FIG. 3G occurs after the seat device 326 outputs the position adjustment instruction in FIG. 3E and the passenger 387 adjusts the passenger's facing direction. In FIG. 3G, the passenger 387 has adjusted the passenger's position toward the target 380 since the output of the adjustment instruction in FIG. 3E. However, the passenger 387 faces a current facing direction 384C that still does not align or substantially align with the target facing direction 382. In the example of FIG. 3G, a passenger-to-target angle $\theta_{PT3}$ between the current facing direction 384C of the passenger 387 and the target facing direction 382 is −15 degrees. Hence, after the position adjustment instruction was output in FIG. 3E and the passenger 387 has adjusted the passenger's position, the seat device 326 in FIG. 3G may estimate the current facing direction 384C (e.g., updated facing direction) and determine that the passenger 387 still does not face the target 380 based on the current facing direction 384C and the location of the target 380.

Upon determining that the passenger 387 still does not face the target 380, the seat device 326 may determine an updated position adjustment parameter indicating an updated position adjustment to be made by the passenger 387 to face the target 380, based on the passenger location, the location of the target 380 and the current facing direction 384C (e.g., updated facing direction). For example, the seat device 326 may determine the updated position adjustment parameter to be −15 degrees (e.g., indicated by the passenger-to-target angle $\theta_{PT3}$), which indicates that the passenger 387 needs to turn 15 degrees to the right to face the target 380. Subsequently, in an aspect, the seat device 326 may output a visual instruction on a display screen and/or an audio instruction, based on the updated position adjustment parameter. For example, the seat device 326 may provide a visual instruction displaying "Turn 15 degrees to right" on the display device 330 and/or output an audio instruction with an audio output of "Turn 15 degrees to right".

In certain scenarios, the passenger may end up adjusting the position of the passenger further away from the position to face the target, even after the position adjustment instruction with at least an audio instruction is provided. For example, if the passenger is unable to comprehend the audio instruction, the passenger may not be able to correctly follow the audio instruction to adjust the position to the position to face the target. The passenger's inability to understand the audio instruction may be due to the passenger's hearing impairment and/or the surrounding noise that makes it difficult to hear the audio instruction. In this case, it may be beneficial to test the passenger's hearing capability and the visual capability, to determine what type of position adjustment instruction to provide to improve the passenger's comprehension. Hence, in some aspects, the passenger position guide module 378 of the seat device 326 may determine whether the passenger has adjusted the position of the passenger further away from a position to face the target after the position adjustment instruction is output. When the passenger position guide module 378 determines that the passenger has adjusted the position of the passenger further away from the position to face the target, the passenger capability processing module 370 of the seat device 326 may output a visual and hearing capability test on the display device 330 to test the visual capability as well as a hearing capability of the passenger. The passenger may provide answers to the visual and hearing capability test to the seat device 326, e.g., via an input device such as a touchscreen, a keyboard, and/or buttons. After receiving the answers from the passenger in response to the visual and hearing capability test, the passenger capability processing module 370 of the seat device 326 may determine, based on the answers, a hearing impairment parameter that indicates a degree of hearing impairment of the passenger and may further determine an updated visual impairment parameter of the passenger.

Further, with the passenger's position adjustment/movement after the position adjustment instruction was output, the passenger may face a different direction at this point than prior to the position adjustment instruction. Hence, the passenger position guide module 378 of the seat device 326 may also estimate an updated facing direction toward which the passenger faces after the position adjustment instruction is output. Based on the passenger location, the location of the target, and the updated facing direction, the passenger position guide module 378 may determine an updated position adjustment parameter that indicates an updated position adjustment to be made by the passenger, in order to face the target. Subsequently, the passenger position guide module 370 of the seat device 326 may output an updated position adjustment instruction based on the updated position adjustment parameter. Here, the updated position adjustment instruction may include an updated audio instruction and/or an updated visual instruction, based on the hearing impairment parameter and the updated visual impairment parameter of the passenger.

Hence, in an aspect, for the updated position adjustment instruction, the passenger position guide module 370 may determine whether to output the updated audio instruction or the updated visual instruction or both the updated audio instruction and/or the updated visual instruction, based on the hearing impairment parameter and the updated visual impairment parameter of the passenger. For example, if the hearing impairment parameter indicates severe hearing impairment and/or the updated visual impairment parameter indicates no or little visual impairment, the passenger position guide module 370 may output the updated position adjustment instruction that includes the updated visual instruction, without including an audio instruction. For example, if the updated visual impairment parameter indicates severe hearing impairment and/or the audio impairment parameter indicates no or little audio impairment, the passenger position guide module 370 may output the updated position adjustment instruction that includes the updated audio instruction, without including a visual instruction. For example, if the hearing impairment parameter indicates mild hearing impairment and/or the updated visual impairment parameter indicates mild visual impairment, the passenger position guide module 370 may output the updated position adjustment instruction that includes both the updated audio instruction and the updated visual instruction. Especially for passengers with a mild hearing impairment and a mild visual impairment, providing both the audio instruction and the updated visual instruction may increase the chance of the passenger comprehending the updated position adjustment instruction.

Figure 3H:
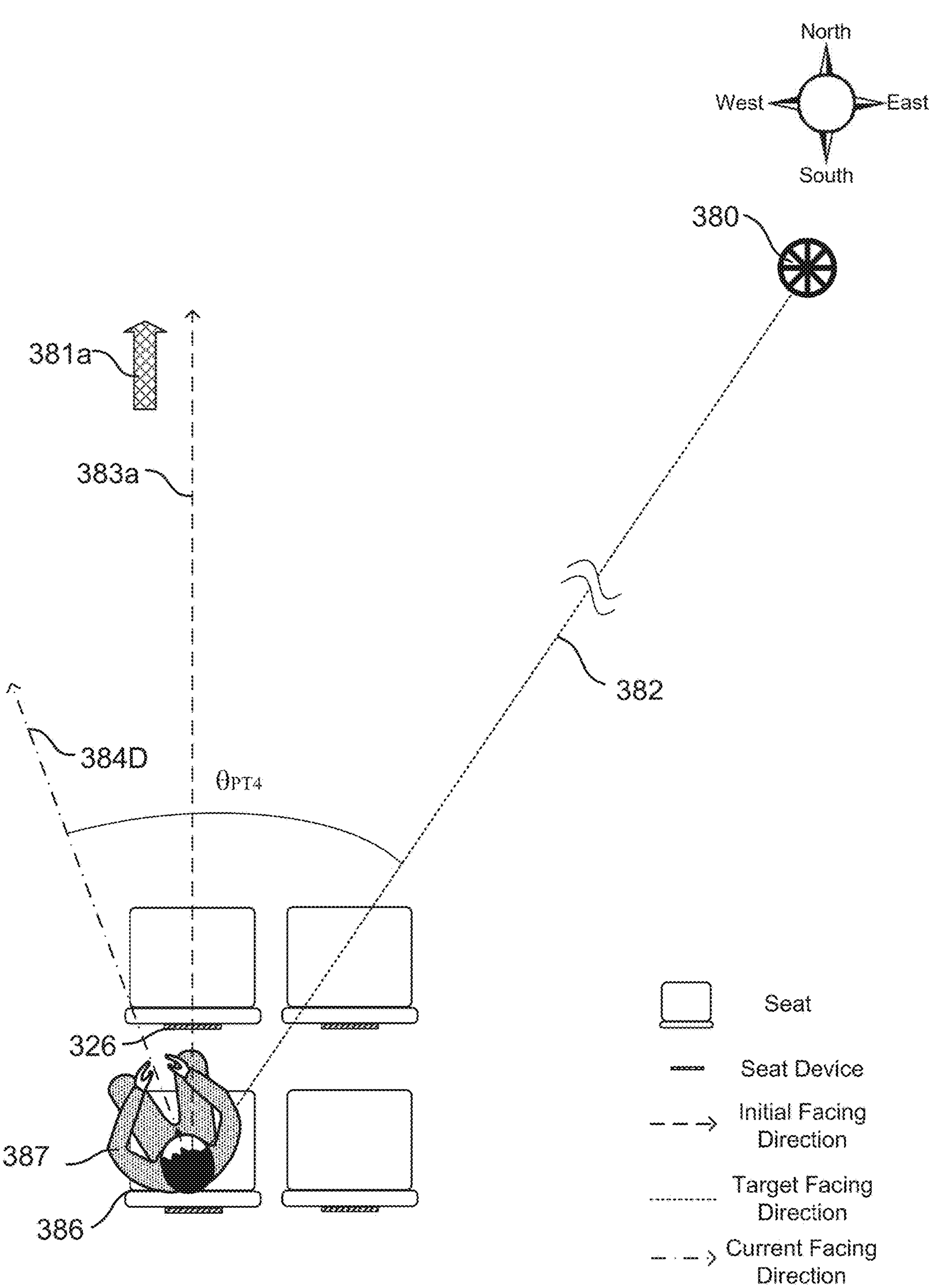
FIG. 3H shows an example diagram showing the passenger of FIG. 3E sitting on the passenger seat with the passenger facing further away from the target, according to some aspects.

FIG. 3H shows an example diagram showing the passenger of FIG. 3E sitting on the passenger seat with the passenger facing further away from the target, according to some aspects. The example shown in FIG. 3H occurs after the seat device 326 outputs the position adjustment instruction in FIG. 3E and the passenger 387 adjusts the passenger's facing direction. In FIG. 3H, the passenger 387 has adjusted the passenger's position further away from the target 380 since the output of the adjustment instruction in FIG. 3E, and thus faces a current facing direction 384D that does not align with the target facing direction 382. In the example of FIG. 3H, a passenger-to-target angle $\theta_{PT4}$ between the current facing direction 384D of the passenger 387 and the target facing direction 382 is −50 degrees. Hence, after the position adjustment instruction was output in FIG. 3E and the passenger 387 has adjusted the passenger's position, the seat device 326 in FIG. 3H may determine (e.g., based on the current facing direction 384D) that the passenger 387 has adjusted the passenger's position further away from the target facing position 382. This may indicate that the passenger 387 is unable to comprehend audio instructions, and thus additional testing of the passenger's capability may be beneficial.

Accordingly, upon determining that the passenger 387 has adjusted the passenger's position further away from the target facing position 382, the seat device 326 may output a visual and hearing capability test on a display screen to test the visual capability and a hearing capability of the passenger. After receiving answers to the visual and hearing capability test from the passenger 387, the seat device 326 may determine a hearing impairment parameter indicating a degree of hearing impairment of the passenger 387 and an updated visual impairment parameter of the passenger 387 based on the received answers.

After determining that the passenger 387 has adjusted the passenger's position further away from the target facing position 382, the seat device 326 may estimate an updated facing direction toward which the passenger faces. Subsequently, the seat device 326 may determine an updated position adjustment parameter indicating an updated position adjustment to be made by the passenger 387 to face the target 380, based on the passenger location, the location of the target 380, and the current facing direction 384C (e.g., updated facing direction). For example, the seat device 326 may determine the updated position adjustment parameter to be −50 degrees (e.g., as shown by the passenger-to-target angle $\theta_{PT4}$), which indicates that the passenger 387 needs to turn 50 degrees to the right to face the target 380. Subsequently, in an aspect, the seat device 326 may an updated position adjustment instruction based on the updated position adjustment parameter, where the updated position adjustment instruction includes an updated audio instruction or an updated visual instruction or both the updated audio instruction or the updated visual instruction. For example, the seat device 326 may determine whether to provide the updated audio instruction or the updated visual instruction or both the updated audio instruction or the updated visual instruction, based on the hearing impairment parameter and the updated visual impairment parameter of the passenger 387. Based on this determination, the seat device 326 may provide a visual instruction displaying "Turn 50 degrees to right" on the display device 330 and/or output an audio instruction with an audio output of "Turn 50 degrees to right".

In some aspects, a visual capability test may include a test for the passenger facing a left side with respect to the seat device 326, a test for the passenger facing the seat device 326, and a test for the passenger facing a right side with respect to the seat device 326. For example, the seat device 326 may instruct the passenger to face the left side and then perform a test, may instruct the passenger to face the seat device 326 and then perform a test, and may instruct the passenger to face the right side and then perform a test. Depending on which direction the passenger is facing with respect to the seat device 326, there may be an optimal way to convey the position adjustment instruction. Each test may include different forms of visual instructions (e.g., in different shapes and/or different colors and/or different patterns). Based on the results of the visual capability test, a respective visual form of the position adjustment instruction may be output depending on a direction the passenger is facing with respect to the seat device 326. For example, in a scenario where the test for the passenger facing the left side indicates that a large bold font provides the optimal result and the test for the passenger facing the right side indicates that a bright red color font provides the optimal result, then the seat device 326 may output the position adjustment instruction in a large bold font on the display device 330 if the passenger is facing the left side, and may output the position adjustment instruction in the bright red color font if the passenger is facing the right side on the display device 330.

In some aspects, in addition to the visual capability test, the seat device 326 may test the passenger with a hearing capability test that includes a test for the passenger facing a left side with respect to the seat device 326, a test for the passenger facing the seat device 326, and a test for the passenger facing a right side with respect to the seat device 326.

In an example, the passenger may have different degrees of visual impairment between two eyes of the passenger and/or may have different degrees of hearing impairment between two ears of the passenger. In a case where the passenger's left ear has no impairment and the passenger's right ear has a severe hearing impairment, if the passenger is facing the left side with respect to the seat device, the passenger's left ear is farther from the speaker of the seat device and the passenger's right ear is closer to the speaker, and thus the passenger may not be able to hear well due to the left ear being farther from the speaker. In a case where the passenger's left eye has no impairment and the passenger's right eye has a severe visual impairment, if the passenger is facing a left side with respect to the seat device, the passenger's left eye is farther from the display device of the seat device and the passenger's right eye is closer to the display screen, and thus the passenger may not be able to comprehend a visual instruction well due to the left eye being farther from the display device.

Hence, for example, if the test for the passenger facing the left side with respect to the seat device 326 indicates that the degree of visual impairment is high, this test result may indicate that the passenger's right eye is visually impaired. Similarly, if the test for the passenger facing the right side with respect to the seat device 326 indicates that the degree of visual impairment is high, this test result may indicate that the passenger's left eye is visually impaired. Further, if the test for the passenger facing the left side with respect to the seat device 326 indicates that the degree of visual impairment is low or zero, this test result may indicate that the passenger's right eye is not visually impaired. Similarly, if the test for the passenger facing a right side with respect to the seat device 326 indicates that the degree of visual impairment is low or zero, then this test result may indicate that the passenger's left eye is not visually impaired. Hence, if the test for the passenger facing the left side with respect to the seat device 326 indicates that the degree of visual impairment is high and if the test for the passenger facing the right side with respect to the seat device 326 indicates that the degree of visual impairment is low or zero, the seat device 326 may output the position adjustment instruction at least in audio when the passenger is facing the left side and may output the position adjustment instruction in a visual format when the passenger is facing the right side. Similarly, if the test for the passenger facing the left side with respect to the seat device 326 indicates that the degree of visual impairment is low or zero and if the test for the passenger facing the right side with respect to the seat device 326 indicates that the degree of visual impairment is high, the seat device 326 may output the position adjustment instruction in a visual format when the passenger is facing the left side and may output the position adjustment instruction at least in audio when the passenger is facing the right side.

Figure 3I:
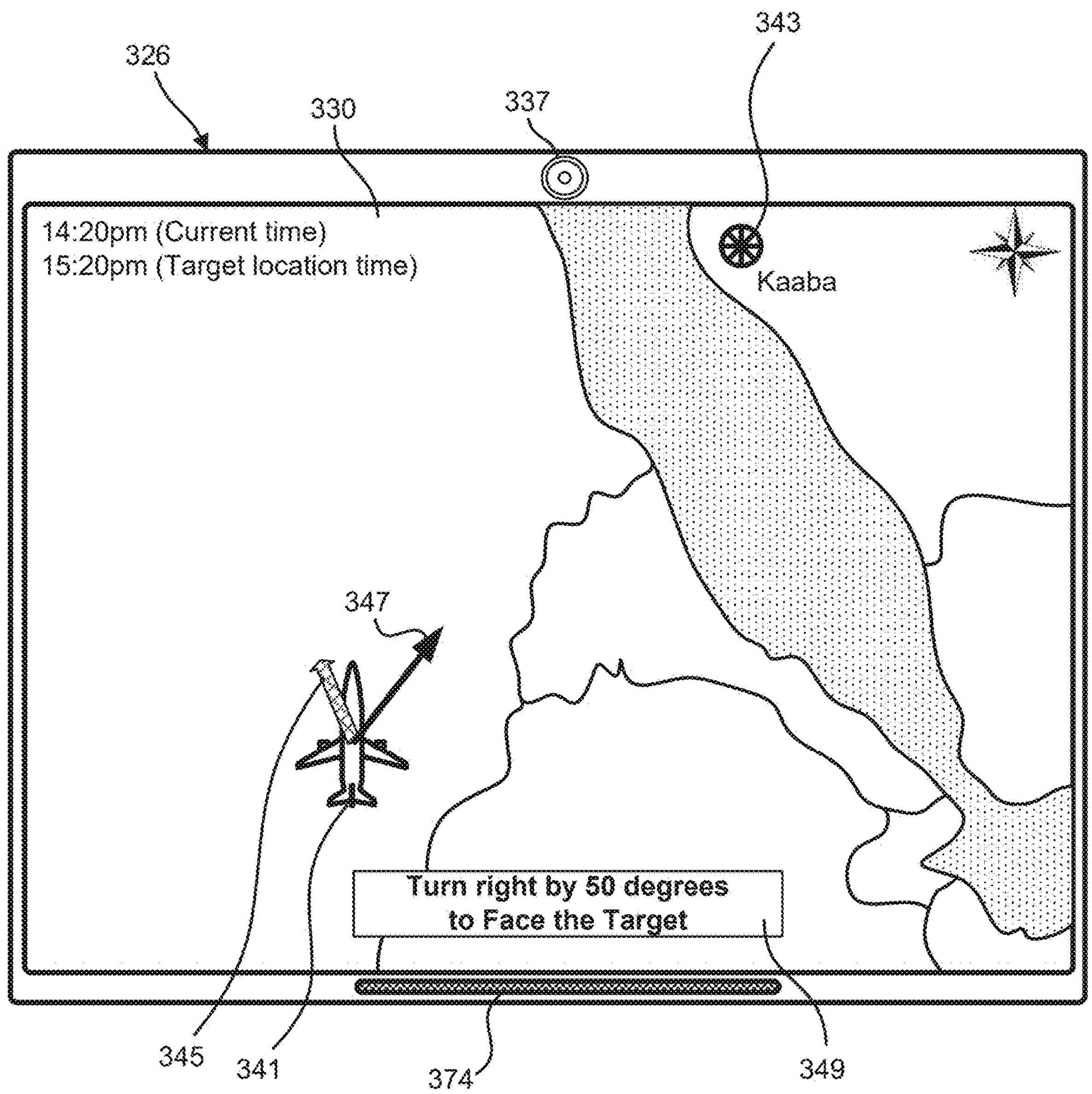
FIG. 3I shows an example of the seat device in a transportation vehicle, according to some aspects.

FIG. 3I shows an example of the seat device 326 in a transportation vehicle, according to some aspects. The seat device 326 shown in FIG. 3I may be the seat device 326 shown in FIG. 3B that is displaying additional information. While the example of FIG. 3B shows the seat device 326 not providing a position adjustment instruction, the example of FIG. 3I shows the seat device 326 providing a position adjustment instruction based on position adjustment parameter indicating a position adjustment to be made by a passenger of a passenger seat to face the Kaaba. In the example of FIG. 3I, the display device 330 of the seat device 326 displays the airplane icon 341 on the map showing a current location and a travel direction of an airplane, and further displays a target icon 343 displaying the Kaaba, which are also shown in the example of FIG. 3B. The airplane icon 341 indicates that the travel direction of the airplane is north, and the target icon 343 indicates that the Kaaba is at northeast of the airplane. The display device 330 also displays the qibla 347, showing the direction toward the Kaaba. Additionally, the display device 330 displays a current facing direction icon 345 indicating a current direction in which the passenger is facing. The current facing direction icon 345 may be updated regularly to reflect a current direction in which the passenger is facing. As discussed above, the current facing direction may be estimated by one or more images of the passenger captured by the camera 337.

In the example shown in FIG. 3I, the seat device 326 has determined that the position adjustment parameter is −55 degrees, and thus may output a position adjustment instruction "Turn right by 50 degrees" in audio based on the position adjustment parameter, via the speaker 374 and/or via a headset wirelessly connected to the seat device 326. In an example, the seat device 326 may also output additional information in audio, such as the flying direction (e.g., "the airplane is currently flying in a north direction") and the relative location of the Kaaba (e.g., "the Kaaba is located in northeast of the airplane" or "the Kaaba is located to your right"). Because the position adjustment instruction is provided in audio, a visually impaired passenger may be able to comprehend which direction he or she will need to move to face the Kaaba. The display device 330 may also display a visual instruction 349 of the position adjustment instruction. For example, for a passenger with visual and hearing impairments, providing the position adjustment instruction in both audio and video may help the passenger comprehend the position adjustment instruction.

Further, the display device 330 may display a current time and a target location time that is a time at the location of the target. For example, a Muslim passenger may want to know the time at the location of the Kaaba, to determine whether it is a time to face the Kaaba and pray. In one example, the seat device 326 may be configured such that the seat device 326 can provide a notification when it is time to face the Kaaba and pray. Such a notification may be provided in audio via the speaker 374 and/or via a headset wirelessly connected to the seat device 326, and/or may be provided visually on the display device 330.

Figure 3J:
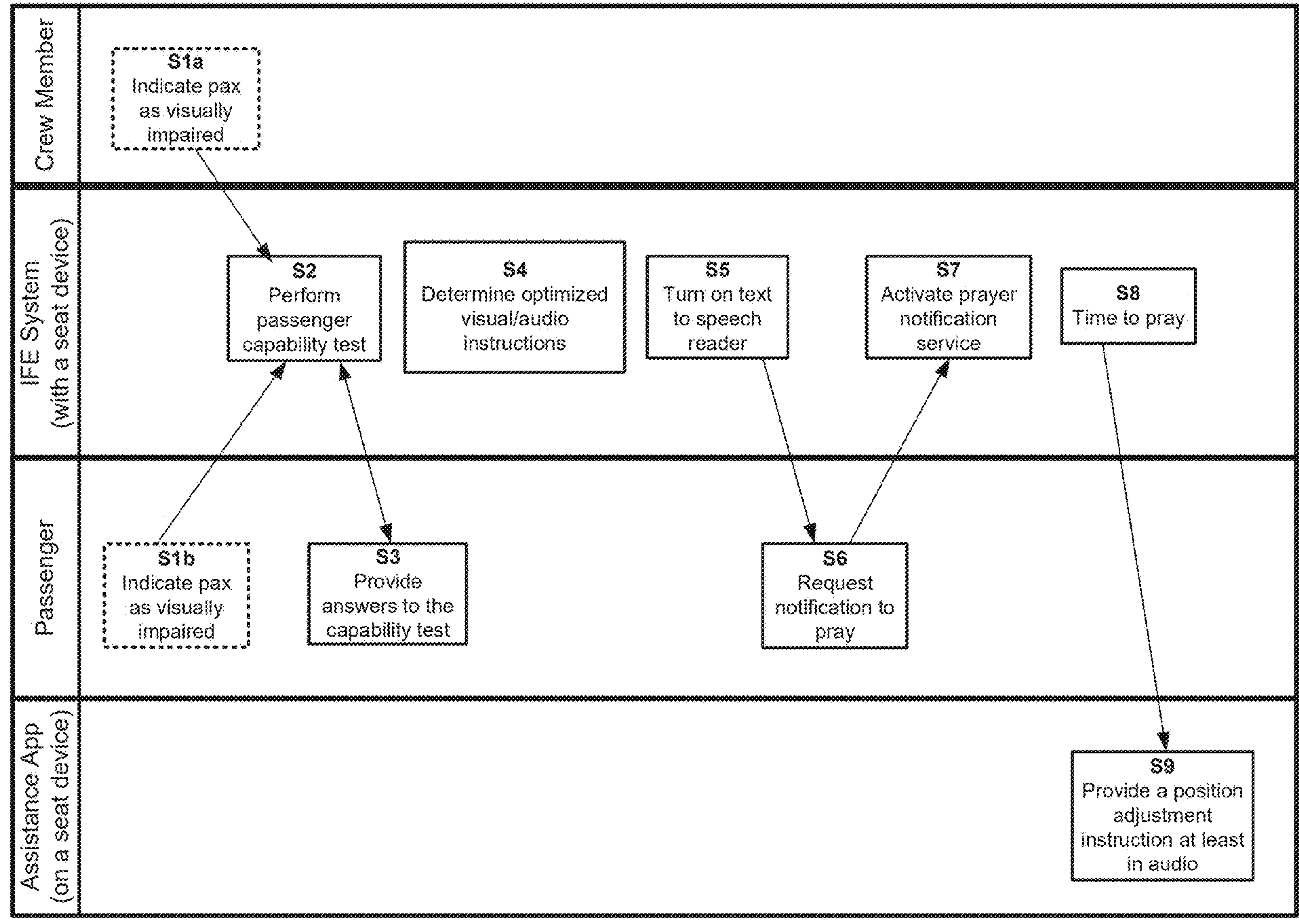
FIG. 3J is an example diagram showing an example application of a position adjustment instruction in audio for a passenger in a transportation vehicle such as an aircraft, according to some aspects.

FIG. 3J is an example diagram showing an example application of a position adjustment instruction in audio for a passenger in a transportation vehicle such as an aircraft, according to some aspects. At S1*a*, a crew member of the aircraft may learn from a passenger or passenger data provided by the passenger that the passenger is visually impaired and thus indicate the passenger as visually impaired to an IFE system having a seat device (e.g., seat device 326). Additionally or alternatively, at S1*b*, the passenger may indicate to the IFE system that the passenger is visually impaired, e.g., by selecting an option for the visual impairment on the seat device 326. At S2, the seat device 326 may provide a passenger capability test, such as a visual capability test, and at S3, the passenger may provide answers in response to the passenger capability test. At S4, the seat device 326 may determine what type of position adjustment instruction to provide, an audio instruction, a visual instruction, or both the audio instruction and the visual instruction, based on the passenger's answers. In this example, the seat device 326 has determined that the passenger has visual impairment. Hence, at S5, the seat device 326 turns on a text-to-speech reader software to provide the audio instruction of the position adjustment instruction and may notify the passenger that the audio instruction will be provided. At S6, the passenger may request a notification to pray, e.g., by selecting a prayer notification option on the seat device 326. Subsequently, at S7, the seat device 326 activates a prayer notification service. With the prayer notification service activated, when it is time to pray, at S8, the seat device 326 outputs a position adjustment instruction at least in audio (e.g., via the text-to-speech reader software) using an assistance application, where the position adjustment instruction indicates which direction the passenger needs to turn to face the Kaaba.

Process Flow

Figure 4B:
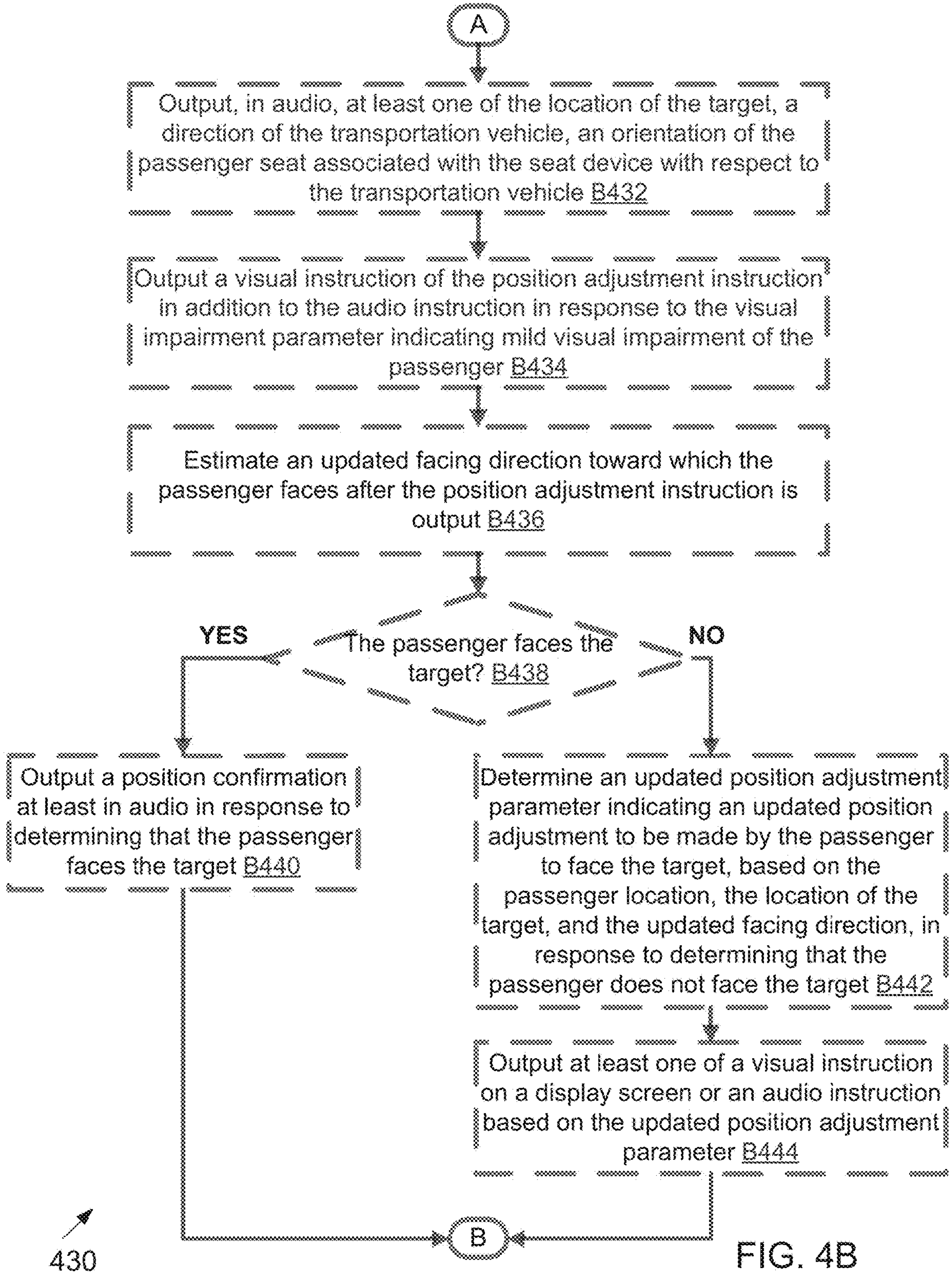
FIG. 4B shows a process by the seat device of the transportation vehicle for providing an instruction for the passenger to make a position adjustment, according to one aspect of the present disclosure.

FIGS. 4A-4D show processes for providing an instruction for a passenger to make a position adjustment, according to some aspects of the present disclosure. FIG. 4A shows a process 400 by a seat device of a transportation vehicle for providing an instruction for a passenger to make a position adjustment, according to one aspect of the present disclosure. The process 400 may be performed by a seat device associated with a passenger seat where the passenger sits, such as the seat device 326 shown in FIG. 3A, 3B, 3E, 3F, 3G, 3H, or 3I. In an example, the process 400 may be performed by a processor (e.g., processor 332) of the seat device 326.

Process 400 may begin with block 402, where the seat device 326 may output a visual capability test on a display screen (e.g., display device 330) to test a visual capability of the passenger. Then, at block 404, the seat device 326 may receive one or more answers from the passenger in response to the visual capability test. As discussed above, the testing data structure 368 and the passenger capability processing module may be used to output the visual passenger capability test and to receive and process answers from the passenger in response to the visual capability test. The answers from the passenger in response to the visual capability test may indicate the visual capability or the visual impairment of the passenger, and thus the answers may be used to determine an optimal form of an instruction to provide to the passenger.

Alternatively or additionally, in block 406, the seat device 326 may receive passenger impairment information of the passenger, the passenger impairment information indicating the degree of visual impairment of the passenger. As discussed above, the data may store the passenger impairment information of the passenger, which may be provided prior to departure of the transportation vehicle. With the passenger impairment information, the seat device 326 may have information to consider when determining an optimal form of an instruction to provide to the passenger.

In block 408, the seat device 326 may capture one or more images of the passenger using a camera device (e.g., camera 337). As discussed above, the camera 337 may be used to capture the one or more images of the passenger, such that the passenger position guide module 378 may utilize the one or more images to estimate a facing direction of the passenger. This provides a simple approach that allows the seat device 326 to regularly estimate the facing direction by simply capturing images and processing the captured images.

In block 410, the seat device 326 may receive a passenger orientation data from a mobile device associated with the passenger. As discussed above, the seat device communication interface 328 may utilize the seat device communication interface 328 to receive the passenger orientation data from PED 302.

In block 412, the seat device 326 determines a visual impairment parameter indicating a degree of visual impairment of a passenger of a passenger seat associated with the seat device. As discussed above, the passenger capability processing module 370 may determine the visual impairment parameter. In some aspects, the visual impairment parameter may be determined based on the one or more answers (e.g., received at block 404) from the passenger in response to the visual capability test. In some aspects, the visual impairment parameter may be determined based on the passenger impairment information (e.g., received at block 406).

In block 414, the seat device 326 determines a passenger location of the passenger and a location of a target. As discussed above, the passenger position guide module 378 of the seat device 326 may determine the location of the target.

In block 416, the seat device 326 estimates an initial facing direction toward which the passenger faces. As discussed above, the passenger position guide module 378 of the seat device 326 may estimate the initial facing direction. In some aspects, the initial facing direction may be estimated based on at least one of a direction of the transportation vehicle or an orientation of the passenger seat associated with the seat device with respect to the transportation vehicle. In some aspects, the initial facing direction may be estimated based on the one or more images of the passenger (e.g., captured at block 408) and a direction of the transportation vehicle. In some aspects, the initial facing direction may be estimated based on the passenger orientation data (received at block 410).

In block 418, the seat device 326 determines a position adjustment parameter indicating a position adjustment to be made by the passenger of the passenger seat to face the target, based on the passenger location, the location of the target, and the initial facing direction. As discussed above, the passenger position guide module 378 may determine the position adjustment parameter.

In block 420, the seat device 326 outputs a position adjustment instruction according to the position adjustment parameter, the position adjustment instruction including at least an audio instruction in response to the visual impairment parameter indicating visual impairment of the passenger. As discussed above, the passenger position guide module 378 may output the position adjustment instruction at least in audio (via the speaker 374 or via a headset connected to the seat device 326) when the visual impairment parameter indicates that the passenger is visually impaired. By providing an audio instruction, a visually impaired passenger may be able to comprehend the position adjustment instruction better than when only a visual instruction is provided.

In some aspects, the visual capability test may include a first test for the passenger facing a left side with respect to the seat device, a second test for the passenger facing the seat device, and a third test for the passenger facing a right side with respect to the seat device. In this aspect, the outputting of the position adjustment instruction in block 420 may include outputting the position adjustment instruction in a visual form, the visual form being based on the initial facing direction with respect to the seat device and based on the first test, the second test, and the third test.

FIG. 4B shows a process 430 by the seat device of the transportation vehicle for providing an instruction for the passenger to make a position adjustment, according to one aspect of the present disclosure. The process 430 of FIG. 4B may continue from the process 400 of FIG. 4A.

In block 432, the seat device 326 may output, in audio, at least one of the location of the target, a direction of the transportation vehicle, an orientation of the passenger seat associated with the seat device with respect to the transportation vehicle. As discussed above, the passenger position guide module 378 may output, in audio (e.g., via the speaker 374 or via a headset connected to the seat device 326), the location of the target, the direction of the transportation vehicle, and/or the orientation of the passenger seat associated with the seat device with respect to the transportation vehicle. Providing this information in audio in addition to the position adjustment instruction may help a visually impaired passenger better understand how the passenger needs to adjust the position of the passenger to face the target.

In block 434, the seat device 326 may output a visual instruction of the position adjustment instruction in addition to the audio instruction in response to the visual impairment parameter indicating mild visual impairment of the passenger. As discussed above, the passenger position guide module 378 of the seat device 326 may output the visual instruction of the position adjustment instruction in addition to the audio instruction. By providing the visual instruction in addition to the audio instruction, the passenger may be able to try to comprehend the position adjustment instruction using both the visual instruction and the audio instruction.

In block 436, the seat device 326 may estimate an updated facing direction toward which the passenger faces after the position adjustment instruction is output. In block 438, the seat device 326 may determine whether the passenger faces the target based on the passenger location, the updated facing direction, and the location of the target. As discussed above, after the position adjustment instruction is output (e.g., in block 420), the passenger position guide module 378 of the seat device 326 may estimate the updated facing direction toward which the passenger faces and may determine whether the passenger faces the target based on the passenger location, the updated facing direction, and the location of the target. By regularly estimating the updated facing direction after outputting the position adjustment instruction, the seat device 326 can ensure that the passenger is facing the target.

In block 440, the seat device 326 may output a position confirmation at least in audio in response to determining that the passenger faces the target. As discussed above, if the passenger position guide module 378 determines that the passenger faces the target, the passenger position guide module 378 may output the position confirmation at least in audio, to confirm that the passenger is in a position that faces the target.

In block 442, the seat device 326 may determine an updated position adjustment parameter indicating an updated position adjustment to be made by the passenger to face the target, based on the passenger location, the location of the target, and the updated facing direction, in response to determining that the passenger does not face the target. In block 444, the seat device 326 may output at least one of a visual instruction on a display screen or an audio instruction based on the updated position adjustment parameter. As discussed above, if the passenger position guide module 378 of the seat device 326 determines that the passenger is not facing the target, the passenger position guide module 378 may determine an updated position adjustment parameter indicating an updated position adjustment to be made by the passenger to face the target, based on the passenger location, the location of the target, and the updated facing direction. Further, as discussed above, the passenger position guide module 378 may output the visual instruction or the audio instruction or both the visual instruction or the audio instruction based on the updated position adjustment parameter. If the passenger is not yet facing the target even after the position adjustment instruction was provided to the passenger, it may be beneficial to figure out the updated position adjustment parameter that can be used to provide an instruction on adjusting the passenger's position to face the target.

FIG. 4C shows a process 460 by the seat device of the transportation vehicle for providing an instruction for the passenger to make a position adjustment, according to one aspect of the present disclosure. In some aspects, the process 460 of FIG. 4C may continue from the process 430 of FIG. 4B. In some aspects, the process 460 of FIG. 4C may continue from the process 400 of FIG. 4A.

In block 462, the seat device 326 may determine that the passenger has adjusted the position of the passenger further away from a position to face the target after the position adjustment instruction is output. As discussed above, the passenger position guide module 378 of the seat device 326 may determine whether the passenger has adjusted the position of the passenger further away from a position to face the target after the position adjustment instruction is output.

In block 464, the seat device 326 may output a visual and hearing capability test on a display screen to test the visual capability and a hearing capability of the passenger in response to the position of the passenger being adjusted further away from the position to face the target. In block 466, the seat device 326 may receive at least one answer from the passenger in response to the visual and hearing capability test. As discussed above, when the passenger position guide module 378 determines that the passenger has adjusted the position of the passenger further away from the position to face the target, the passenger capability processing module 370 of the seat device 326 may output a visual and hearing capability test on the display device 330 to test the visual capability as well as a hearing capability of the passenger, and may receive answers in response.

In block 468, the seat device 326 may determine a hearing impairment parameter indicating a degree of hearing impairment of the passenger and an updated visual impairment parameter of the passenger based on the at least one answer. As discussed above, the passenger capability processing module 370 of the seat device 326 may determine, based on the passenger's answers to the visual and hearing capability test, the hearing impairment parameter and the updated visual impairment parameter of the passenger. For example, if the passenger is adjusting the position away from the target even after the position adjustment instruction was provided in audio, then it is possible that the passenger may have a hearing impairment. Therefore, it may be beneficial to have the passenger take the visual and hearing capability test and figure out the degree of the passenger's hearing impairment and also figure out again the degree of the passenger's visual impairment, to be able to provide an optimal form of a position adjustment instruction.

In block 470, the seat device 326 may estimate an updated facing direction toward which the passenger faces after the position adjustment instruction is output. As discussed above, the passenger position guide module 378 of the seat device 326 may estimate the passenger location and the updated facing direction.

In block 472, the seat device 326 may determine an updated position adjustment parameter indicating an updated position adjustment to be made by the passenger to face the target, based on the passenger location, the location of the target, and the updated facing direction. As discussed above, the passenger position guide module 378 may determine the updated position adjustment parameter based on the passenger location, the location of the target, and the updated facing direction.

In block 474, the seat device 326 may output an updated position adjustment instruction based on the updated position adjustment parameter, wherein the updated position adjustment instruction includes at least one of an updated audio instruction or an updated visual instruction, based on the hearing impairment parameter and the updated visual impairment parameter of the passenger. As discussed above, the passenger position guide module 370 of the seat device 326 may output an updated position adjustment instruction based on the updated position adjustment parameter. Here, both the hearing impairment parameter and the updated visual impairment parameter of the passenger may be considered to determine a type of the updated position adjustment instruction, the type being the audio instruction, the visual instruction, or both the audio instruction and the video instruction.

Figure 4D:
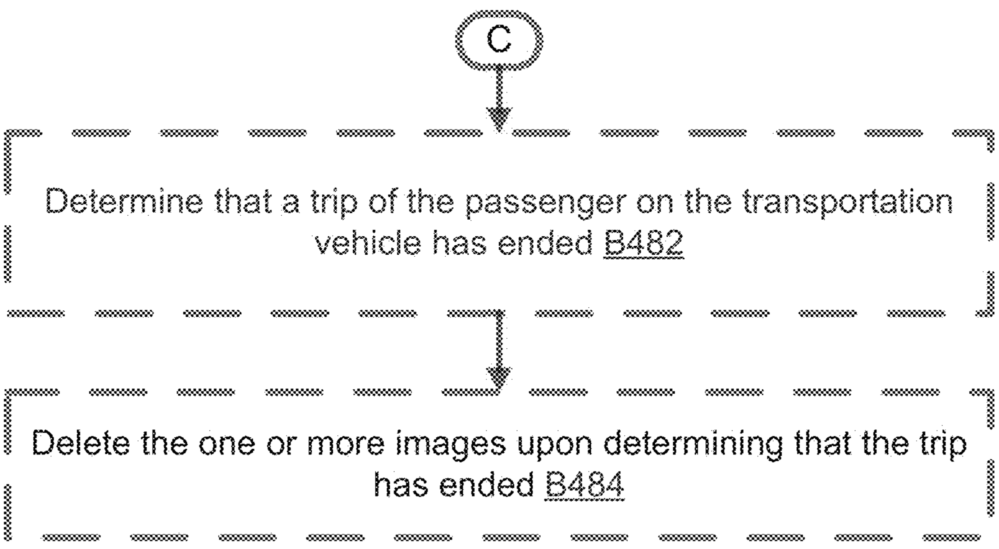
FIG. 4D shows a process by the seat device of the transportation vehicle for providing an instruction for the passenger to make a position adjustment, according to one aspect of the present disclosure.
Figure 4D:

FIG. 4D shows a process 480 by the seat device of the transportation vehicle for providing an instruction for the passenger to make a position adjustment, according to one aspect of the present disclosure. In some aspects, the process 480 of FIG. 4D may continue from the process 460 of FIG. 4C. In some aspects, the process 480 of FIG. 4D may continue from the process 430 of FIG. 4B. In some aspects, the process 480 of FIG. 4D may continue from the process 400 of FIG. 4A.

In block 482, the seat device 326 may determine that a trip of the passenger on the transportation vehicle has ended. In block 484, the seat device 326 may delete the one or more images upon determining that the trip has ended. As discussed above, when a trip of the passenger on the transportation vehicle ends, the passenger position guide module 378 of the seat device 326 may delete the one or more images upon determining that the trip has ended. Deleting the images captured by the camera 337 at the end of the trip may help protecting the privacy of the passenger.

Processing System

Figure 5:
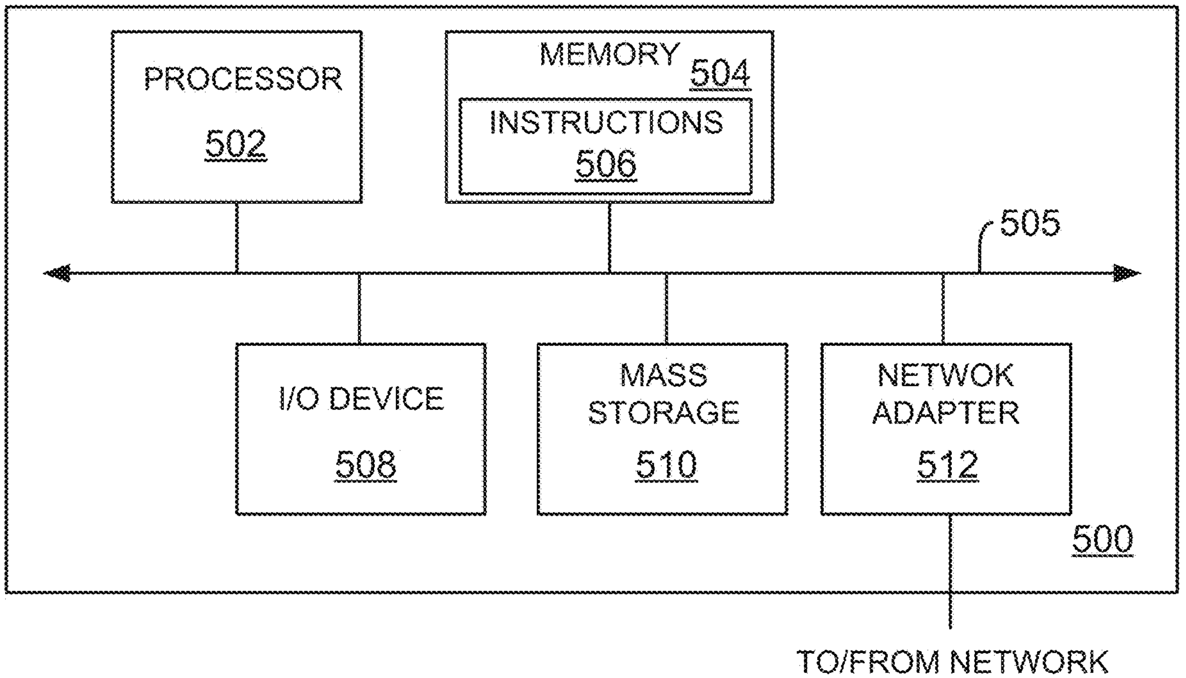
FIG. 5 shows a block diagram of a computing system, used according to one aspect of the present disclosure.

FIG. 5 is a high-level block diagram showing an example of the architecture of a processing system 500 that may be used according to one aspect. The processing system 500 can represent CMD 360, media server 112, computing system 106/107, WAP 130, onboard management system 344, seat device 326 or any user device (PED 302) that attempts to interface with a vehicle computing device. Note that certain standard and well-known components which are not germane to the present aspects are not shown in FIG. 5.

The processing system 500 includes one or more processor(s) 502 and memory 504, coupled to a bus system 505. The bus system 505 shown in FIG. 5 is an abstraction that represents any one or more separate physical buses and/or point-to-point connections, connected by appropriate bridges, adapters and/or controllers. The bus system 505, therefore, may include, for example, a system bus, a Peripheral Component Interconnect (PCI) bus, a HyperTransport or industry standard architecture (ISA) bus, a small computer system interface (SCSI) bus, a universal serial bus (USB), or an Institute of Electrical and Electronics Engineers (IEEE) standard 1394 bus (sometimes referred to as "Firewire") or any other interconnect type.

The processor(s) 502 are the central processing units (CPUs) of the processing system 500 and, thus, control its overall operation. In certain aspects, the processors 502 accomplish this by executing software stored in memory 504. A processor 502 may be, or may include, one or more programmable general-purpose or special-purpose microprocessors, digital signal processors (DSPs), programmable controllers, application specific integrated circuits (ASICs), programmable logic devices (PLDs), or the like, or a combination of such devices.

Memory 504 represents any form of random-access memory (RAM), read-only memory (ROM), flash memory, or the like, or a combination of such devices. Memory 504 includes the main memory of the processing system 500. Instructions 506 may be used to the process steps of FIG. 4A-4D executed by the modules 370, 372, and 378 as well as the data structure 368, described above.

Also connected to the processors 502 through the bus system 505 are one or more internal mass storage devices 510, and a network adapter 512. Internal mass storage devices 510 may be or may include any conventional medium for storing large volumes of data in a non-volatile manner, such as one or more magnetic or optical based disks, flash memory, or solid-state drive.

The network adapter 512 provides the processing system 500 with the ability to communicate with remote devices (e.g., over a network) and may be, for example, an Ethernet adapter or the like.

The processing system 500 also includes one or more input/output (I/O) devices 508 coupled to the bus system 505. The I/O devices 508 may include, for example, a display device, a keyboard, a mouse, etc. The I/O device may be in the form of a handset having one or more of the foregoing components, such as a display with a real or virtual keyboard, buttons, and/or other touch-sensitive surfaces.

Thus, methods and systems for providing an instruction for a passenger to make a position adjustment have been described. Note that references throughout this specification to "one aspect" (or "embodiment") or "an aspect" mean that a particular feature, structure or characteristic described in connection with the aspect is included in at least one aspect of the present disclosure. Therefore, it is emphasized and should be appreciated that two or more references to "an aspect" or "one aspect" or "an alternative aspect" in various portions of this specification are not necessarily all referring to the same aspect. Furthermore, the particular features, structures or characteristics being referred to may be combined as suitable in one or more aspects of the disclosure, as will be recognized by those of ordinary skill in the art.

While the present disclosure is described above with respect to what is currently considered its preferred aspects, it is to be understood that the disclosure is not limited to that described above. To the contrary, the disclosure is intended to cover various modifications and equivalent arrangements within the spirit and scope of the appended claims.

What is claimed is:

1. A method executed by a seat device of a transportation vehicle, comprising:

determining by a passenger capability processing module of the seat device, based on passenger-related data received by the seat device, a visual impairment parameter indicating a degree of visual impairment of a passenger of a passenger seat associated with the seat device;

determining by a passenger position guide module of the seat device, based on location sensor data received from a location sensor connected to the seat device, a passenger location of the passenger;

estimating by the passenger position guide module, based on data received from at least one of a passenger orientation measuring device or an image capturing device, an initial facing direction toward which the passenger faces;

determining, by the passenger position guide module, a position adjustment parameter indicating a position adjustment to be made by the passenger of the passenger seat to face a target, based on the passenger location, a location of the target, and the initial facing direction;

outputting, via at least an audio output device, a position adjustment instruction according to the position adjustment parameter, the position adjustment instruction including at least an audio instruction in response to the visual impairment parameter indicating visual impairment of the passenger;

iteratively updating, by the passenger position guide module, the position adjustment parameter based on one or more detected changes in a facing direction toward which the passenger faces until the facing direction is within a predetermined range from the location of the target; and outputting, via the at least the audio output device, an updated position adjustment instruction according to the updated position adjustment parameter, the updated position adjustment instruction including at least an updated audio instruction in response to the visual impairment parameter indicating visual impairment of the passenger.

2. The method of claim 1, further comprising:

outputting a visual instruction of the position adjustment instruction in addition to the audio instruction in response to the visual impairment parameter indicating mild visual impairment of the passenger.

3. The method of claim 1, further comprising:

estimating an updated facing direction toward which the passenger faces after the position adjustment instruction is output;

determining whether the passenger faces the target based on the passenger location, the updated facing direction, and the location of the target; and outputting a position confirmation at least in audio in response to determining that the passenger faces the target.

4. The method of claim 3, further comprising:

wherein the iteratively updating the position adjustment parameter comprises determining the updated position adjustment parameter indicating an updated position adjustment to be made by the passenger to face the target, based on the passenger location, the location of the target, and the updated facing direction, in response to determining that the passenger does not face the target; and wherein the method further comprises outputting at least one of a visual instruction on a display screen or an audio instruction based on the updated position adjustment parameter.

5. The method of claim 1, further comprising:

outputting a visual capability test on a display screen to test a visual capability of the passenger; and receiving one or more answers from the passenger in response to the visual capability test, wherein the visual impairment parameter is determined based on the one or more answers from the passenger.

6. The method of claim 5, wherein the visual capability test includes a first test for the passenger facing a left side with respect to the seat device, a second test for the passenger facing the seat device, and a third test for the passenger facing a right side with respect to the seat device, and wherein the outputting the position adjustment instruction comprises outputting the position adjustment instruction in a visual form, the visual form being based on the initial facing direction with respect to the seat device and based on the first test, the second test, and the third test.

7. The method of claim 1, further comprising:

determining that the passenger has adjusted the position of the passenger further away from a position to face the target after the position adjustment instruction is output;

outputting a visual and hearing capability test on a display screen to test the visual capability and a hearing capability of the passenger in response to the position of the passenger being adjusted further away from the position to face the target;

receiving at least one answer from the passenger in response to the visual and hearing capability test;

determining a hearing impairment parameter indicating a degree of hearing impairment of the passenger and an updated visual impairment parameter of the passenger based on the at least one answer;

estimating an updated facing direction toward which the passenger faces after the position adjustment instruction is output;

determining an updated position adjustment parameter indicating an updated position adjustment to be made by the passenger to face the target, based on the passenger location, the location of the target, and the updated facing direction; and outputting an updated position adjustment instruction based on the updated position adjustment parameter, wherein the updated position adjustment instruction includes at least one of an updated audio instruction or an updated visual instruction, based on the hearing impairment parameter and the updated visual impairment parameter of the passenger.

8. The method of claim 1, further comprising:

receiving passenger impairment information of the passenger, the passenger impairment information indicating the degree of visual impairment of the passenger, wherein the visual impairment parameter is determined based on the passenger impairment information.

9. The method of claim 1, wherein the initial facing direction is estimated based on at least one of a direction of the transportation vehicle or an orientation of the passenger seat associated with the seat device with respect to the transportation vehicle.

10. The method of claim 1, further comprising:

capturing one or more images of the passenger using a camera device, wherein the initial facing direction is estimated based on the one or more images of the passenger and a direction of the transportation vehicle.

11. The method of claim 10, further comprising:

determining that a trip of the passenger on the transportation vehicle has ended; and deleting the one or more images upon determining that the trip has ended.

12. The method of claim 1, further comprising:

receiving a passenger orientation data from a mobile device associated with the passenger, wherein the initial facing direction is estimated based on the passenger orientation data.

13. The method of claim 1, further comprising:

outputting, in audio, at least one of the location of the target, a direction of the transportation vehicle, an orientation of the passenger seat associated with the seat device with respect to the transportation vehicle.

14. A non-transitory machine-readable storage medium having stored thereon instructions for performing a method, comprising machine executable code which when executed by at least one machine, causes the machine to:

determine a visual impairment parameter indicating a degree of visual impairment of a passenger of a passenger seat associated with the seat device;

determine a passenger location of the passenger and a location of a target;

estimate an initial facing direction toward which the passenger faces;

determine a position adjustment parameter indicating a position adjustment to be made by the passenger of the passenger seat to face the target, based on the passenger location, the location of the target, and the initial facing direction;

output a position adjustment instruction according to the position adjustment parameter, the position adjustment instruction including at least an audio instruction in response to the visual impairment parameter indicating visual impairment of the passenger; and iteratively update, by the passenger position guide module, the position adjustment parameter based on one or more detected changes in a facing direction toward which the passenger faces until the facing direction is within a predetermined range from the location of the target; and output, via the at least the audio output device, an updated position adjustment instruction according to the updated position adjustment parameter, the updated position adjustment instruction including at least an updated audio instruction in response to the visual impairment parameter indicating visual impairment of the passenger.

15. The non-transitory machine-readable storage medium of claim 14, wherein the machine executable code, when executed by the at least one machine, further causes the machine to:

estimate an updated facing direction toward which the passenger faces after the position adjustment instruction is output;

determine whether the passenger faces the target based on the passenger location, the updated facing direction, and the location of the target; and output a position confirmation at least in audio in response to determining that the passenger faces the target.

16. The non-transitory machine-readable storage medium of claim 15, wherein the machine executable code configured to cause the machine to iteratively update the position adjustment parameter is configured to: determine an updated position adjustment parameter indicating an updated position adjustment to be made by the passenger to face the target, based on the passenger location, the location of the target, and the updated facing direction, in response to determining that the passenger does not face the target; and wherein the machine executable code, when executed by the at least one machine, further causes the machine to output at least one of a visual instruction on a display screen or an audio instruction based on the updated position adjustment parameter.

17. The non-transitory machine-readable storage medium of claim 14, wherein the machine executable code, when executed by the at least one machine, further causes the machine to:

output a visual capability test on a display screen to test a visual capability of the passenger; and receive one or more answers from the passenger in response to the visual capability test, wherein the visual impairment parameter is determined based on the one or more answers from the passenger.

18. The non-transitory machine-readable storage medium of claim 17, wherein the visual capability test includes a first test for the passenger facing a left side with respect to the seat device, a second test for the passenger facing the seat device, and a third test for the passenger facing a right side with respect to the seat device, and wherein the outputting the position adjustment instruction comprises outputting the position adjustment instruction in a visual form, the visual form being based on the initial facing direction with respect to the seat device and based on the first test, the second test, and the third test.

19. The non-transitory machine-readable storage medium of claim 14, wherein the machine executable code, when executed by the at least one machine, further causes the machine to:

determine that the passenger has adjusted the position of the passenger further away from a position to face the target after the position adjustment instruction is output;

output a visual and hearing capability test on a display screen to test the visual capability and a hearing capability of the passenger in response to the position of the passenger being adjusted further away from the position to face the target;

receive at least one answer from the passenger in response to the visual and hearing capability test;

determine a hearing impairment parameter indicating a degree of hearing impairment of the passenger and an updated visual impairment parameter of the passenger based on the at least one answer;

estimate an updated facing direction toward which the passenger faces after the position adjustment instruction is output;

determine an updated position adjustment parameter indicating an updated position adjustment to be made by the passenger to face the target, based on the passenger location, the location of the target, and the updated facing direction; and output an updated position adjustment instruction based on the updated position adjustment parameter, wherein the updated position adjustment instruction includes at least one of an updated audio instruction or an updated visual instruction, based on the hearing impairment parameter and the updated visual impairment parameter of the passenger.

20. A system, comprising:

a memory containing machine readable medium comprising machine executable code having stored thereon instructions; and a processor coupled to the memory to execute the machine executable code to:

determine a visual impairment parameter indicating a degree of visual impairment of a passenger of a passenger seat associated with the seat device;

determine a passenger location of the passenger and a location of a target;

estimate an initial facing direction toward which the passenger faces;

determine a position adjustment parameter indicating a position adjustment to be made by the passenger of the passenger seat to face the target, based on the passenger location, the location of the target, and the initial facing direction;

output a position adjustment instruction according to the position adjustment parameter, the position adjustment instruction including at least an audio instruction in response to the visual impairment parameter indicating visual impairment of the passenger; and iteratively update, by the passenger position guide module, the position adjustment parameter based on one or more detected changes in a facing direction toward which the passenger faces until the facing direction is within a predetermined range from the location of the target; and output, via the at least the audio output device, an updated position adjustment instruction according to the updated position adjustment parameter, the updated position adjustment instruction including at least an updated audio instruction in response to the visual impairment parameter indicating visual impairment of the passenger.

* * * * *